(12) United States Patent
Dalziel et al.

(10) Patent No.: US 8,101,794 B2
(45) Date of Patent: Jan. 24, 2012

(54) CRYSTALLINE FORMS OF A 3-CARBOXYPROPYL-AMINOTETRALIN COMPOUND

(75) Inventors: Sean M. Dalziel, San Francisco, CA (US); Miroslav Rapta, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 19 days.

(21) Appl. No.: 12/633,944

(22) Filed: Dec. 9, 2009

(65) Prior Publication Data

US 2010/0144881 A1  Jun. 10, 2010

Related U.S. Application Data

(60) Provisional application No. 61/121,254, filed on Dec. 10, 2008.

(51) Int. Cl.
| | |
|---|---|
| *C07C 59/00* | (2006.01) |
| *C07C 65/03* | (2006.01) |
| *A01N 37/12* | (2006.01) |
| *A01N 37/44* | (2006.01) |
| *A61K 31/195* | (2006.01) |

(52) U.S. Cl. ........................ 562/471; 514/563
(58) Field of Classification Search ................ None
See application file for complete search history.

(56) References Cited

U.S. PATENT DOCUMENTS

| | | |
|---|---|---|
| 6,498,196 B1 | 12/2002 | Roberts et al. |
| 6,844,368 B1 | 1/2005 | Roberts et al. |
| 2009/0149465 A1 | 6/2009 | Leadbetter et al. |
| 2009/0149535 A1 | 6/2009 | Trapp et al. |
| 2009/0247627 A1 | 10/2009 | Trapp et al. |

OTHER PUBLICATIONS

International Search Report for PCT/US2009/067271, May 2010.
Grundt et al, "Identification of a new scaffold for opioid receptor antagonism based on the 2-amino-1,1-dimethyl-7-hydroxytetralin pharmacophore", J Med Chem, 2004, 5069-5075.
Roy et al., "Synthesis and structure-activity relationship of novel aminotetralin derivatives with high selective opioid affinity", Bioorg & Med Chem Lett, 2002, 12, 3141-3143.
Williams, "Investigation of aminotetralins as novel opioid receptor antagonists", A thesis submitted for the degree of Doctor of Philosophy, University of Bath, May 2006.

*Primary Examiner* — Daniel Sullivan
*Assistant Examiner* — Jennifer C Sawyer
(74) *Attorney, Agent, or Firm* — Jeffrey A. Hagenah; Roberta P. Saxon

(57) ABSTRACT

The invention provides crystalline solid forms of (S)-4-((2S,3S)-7-carbamoyl-1,1 -diethyl-3-methoxy-1,2,3,4-tetrahydronaphthalen-2-ylamino)-2-cyclohexylmethyl-butyric acid. The invention also provides pharmaceutical compositions comprising such crystalline solid forms, methods of using such crystalline solid forms to treat diseases associated with mu opioid receptor activity, and processes useful for preparing such crystalline solid forms.

6 Claims, 5 Drawing Sheets

CRYSTALLINE FORMS OF A 3-CARBOXYPROPYL-AMINOTETRALIN COMPOUND

CROSS-REFERENCE TO RELATED APPLICATIONS

This application claims the benefit of U.S. Provisional Application Nos. 61/121,254, filed on Dec. 10, 2008, the disclosure of which is incorporated herein by reference in its entirety.

BACKGROUND OF THE INVENTION

1. Field of the Invention

The invention is directed to crystalline forms of a 3-carboxypropyl-aminotetralin compound which are useful as mu opioid receptor antagonists. The invention is also directed to pharmaceutical compositions comprising such crystalline compounds, methods of using such compounds for treating or ameliorating medical conditions mediated by mu opioid receptor activity, and processes useful for preparing such compounds.

2. State of the Art

Mu opioid receptor antagonists are expected to be useful for treating or ameliorating medical conditions mediated by mu opioid receptor activity. In particular, peripherally selective mu opioid receptor antagonists are expected to be useful for treating conditions such as opioid-induced bowel dysfunction and postoperative ileus. Commonly-assigned U.S. Provisional Application Nos. 61/007,220, filed Dec. 11, 2007, and 61/049,219, filed Apr. 30, 2008 and U.S. application Ser. No. 12/331,659, filed Dec. 10, 2008, disclose 3-carboxypropyl-aminotetralin compounds. In particular, the compound (S)-4-((2S,3S)-7-carbamoyl-1,1-diethyl-3-methoxy-1,2,3,4-tetrahydronaphthalen-2-ylamino)-2-cyclohexylmethyl-butyric acid (compound 1):

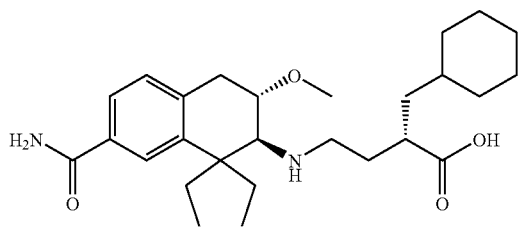

is specifically disclosed in these applications as demonstrating mu opioid receptor antagonist activity.

To effectively use this compound as a therapeutic agent, it would be desirable to have a solid-state form that can be readily manufactured and that has acceptable chemical and physical stability. For example, it would be highly desirable to have a physical form that is thermally stable, for example at temperatures exceeding about 160° C. or about 180° C., and is not deliquescent, thereby facilitating processing and storage of the material. Crystalline solids are generally preferred over amorphous forms, for enhancing purity and stability of the manufactured product.

No crystalline forms of compound 1 have previously been reported. Accordingly, a need exists for a stable, crystalline form of compound 1 that is not deliquescent, and exhibits favorable thermal stability.

SUMMARY OF THE INVENTION

The present invention provides two distinct crystalline solid forms of (S)-4-((2S,3S)-7-carbamoyl-1,1-diethyl-3-methoxy-1,2,3,4-tetrahydronaphthalen-2-ylamino)-2-cyclohexylmethyl-butyric acid (1) and a crystalline hydrochloride salt of compound 1.

Surprisingly, one form of crystalline compound 1 has been found to exhibit no significant thermal events below a temperature of about 162° C. and to exhibit a weight change of less than about 2.5% when exposed to a range of relative humidity between about 2% and about 90% at room temperature. Furthermore, neither crystalline compound 1 nor the crystalline hydrochloride salt of compound 1 is deliquescent when exposed to up to about 90% relative humidity at room temperature.

Among other uses, the crystalline solid forms of the invention are expected to be useful for preparing pharmaceutical compositions for treating or ameliorating medical conditions mediated by mu opioid receptor activity. Accordingly, in another of its composition aspects, the invention provides a pharmaceutical composition comprising a pharmaceutically-acceptable carrier and crystalline (S)-4-((2S,3S)-7-carbamoyl-1,1-diethyl-3-methoxy-1,2,3,4-tetrahydronaphthalen-2-ylamino)-2-cyclohexylmethyl-butyric acid or the present crystalline hydrochloride salt.

The invention also provides a method of treating or ameliorating a disease or condition ameliorated by treatment with a mu opioid receptor antagonist, e.g. a disorder of reduced motility of the gastrointestinal tract, the method comprising administering to the mammal, a therapeutically effective amount of crystalline (S)-4-((2S,3S)-7-carbamoyl-1,1-diethyl-3-methoxy-1,2,3,4-tetrahydronaphthalen-2-ylamino)-2-cyclohexylmethyl-butyric acid (1) or a crystalline hydrochloride salt of compound 1.

The invention further provides a method of treating opioid-induced bowel dysfunction or post-operative ileus, the method comprising administering to the mammal, a therapeutically effective amount of crystalline (S)-4-(2S,3S)-7-carbamoyl-1,1-diethyl-3-methoxy-1,2,3,4-tetrahydronaphthalen-2-ylamino)-2-cyclohexylmethyl-butyric acid (1) or a crystalline hydrochloride salt of compound 1.

In another method aspect, the invention provides a process for preparing a crystalline compound 1 in Form I, the process comprising dispersing (S)-4-((2S,3S)-7-carbamoyl-1,1-diethyl-3-methoxy-1,2,3,4-tetrahydronaphthalen-2-ylamino)-2-cyclohexylmethyl-butyric acid (1) in a polar diluent comprising between about 3% and about 20% water to form a crystallization process mixture; holding the process mixture for at least about 12 hours; and isolating the resulting crystals from the process mixture.

In yet another method aspect, the invention provides a process for preparing crystalline compound 1 in Form I, the process comprising deprotecting the protected intermediate, (S)-4-((2S,3S)-7-carbamoyl-1,1-diethyl-3-methoxy-1,2,3,4-tetrahydronaphthalen-2-ylamino)-2-cyclohexylmethyl-butyric acid benzyl ester by catalytic hydrogenolysis in the presence of a polar diluent comprising between about 10% and about 20% water to form crystalline compound 1.

In related composition aspects, the invention provides (S)-4-((2S,3S)-7-carbamoyl-1,1-diethyl-3-methoxy-1,2,3,4-tetrahydronaphthalen-2-ylamino)-2-cyclohexylmethyl-butyric acid benzyl ester and the bisulfite adduct, sodium; (S)-3-benzyloxycarbonyl-4-cyclohexyl-1-hydroxy-butane-1-sulfonate, which is useful for the preparation of the above protected precursor to compound 1.

The invention also provides crystalline solid forms of the invention as described herein for use in therapy or as a medicament, as well as the use of a crystalline solid form of the invention in the manufacture of a medicament, especially for the manufacture of a medicament for treating a disorder associated with mu opioid receptor activity in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
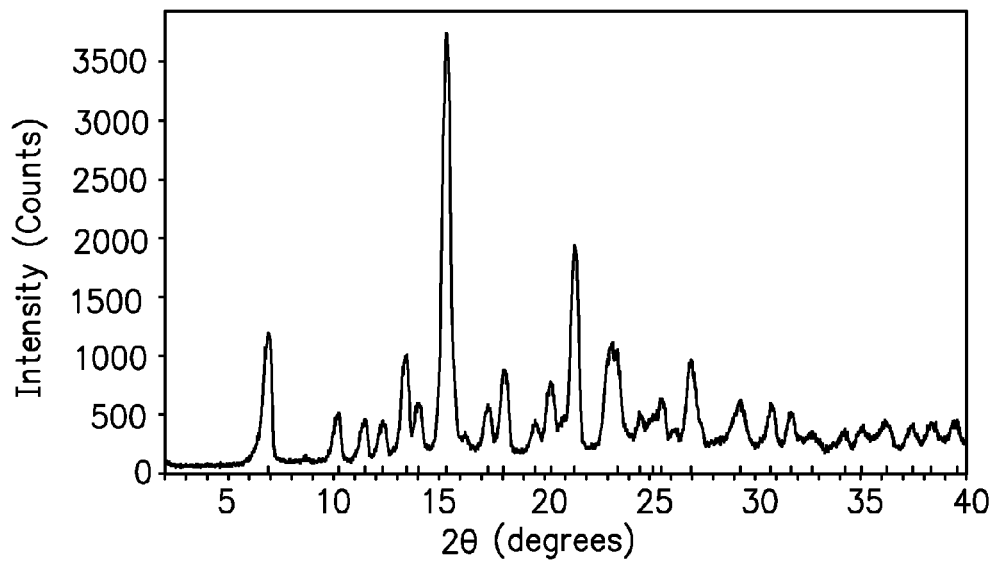
FIG. 1 shows an x-ray powder diffraction (XRPD) pattern of crystalline Form I (S)-4-((2S,3S)-7-carbamoyl-1,1-diethyl-3-methoxy-1,2,3,4-tetrahydronaphthalen-2-ylamino)-2-cyclohexylmethyl-butyric acid of the invention.

The invention provides crystalline solid forms of (S)-4-((2S,3S)-7-carbamoyl-1,1-diethyl-3-methoxy-1,2,3,4-tetrahydronaphthalen-2-ylamino)-2-cyclohexylmethyl-butyric acid (1)

Definitions

When describing the compounds, compositions and methods of the invention, the following terms have the following meanings, unless otherwise indicated.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes, one or more of the following activities:

(a) preventing the disease, disorder, or medical condition from occurring, i.e., prophylactic treatment of a patient;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

It must be noted that, as used in the specification and appended claims, the singular forms "a", "an", "one", and "the" may include plural references, unless the content clearly dictates otherwise.

Naming Convention

Compound 1, is designated (S)-4-((2S,3S)-7-carbamoyl-1,1-diethyl-3-methoxy-1,2,3,4-tetrahydronaphthalen-2-ylamino)-2-cyclohexylmethyl-butyric acid according to the IUPAC conventions as implemented in AutoNom software, (MDL Information Systems, GmbH, Frankfurt, Germany). The bicyclic 1,2,3,4-tetrahydronaphthalen-2-ylamino group is alternatively known by the common name, "aminotetralin".

Crystalline Forms of the Invention

In one aspect, the invention provides crystalline (S)-4-((2S, 3S)-7-carbamoyl-1,1-diethyl-3-methoxy-1,2,3,4-tetrahydronaphthalen-2-ylamino)-2-cyclohexylmethyl-butyric acid (1) in two distinct forms.

In one aspect, Form I crystalline compound 1 is characterized by an x-ray powder diffraction (XRPD) pattern having diffraction peaks at 2θ values of 6.92±0.20 and 15.34±0.20, and two or more diffraction peaks, including three or more and four or more diffraction peaks, at 2θ values selected from 10.24±0.20, 11.48±0.20, 12.32±0.20, 13.46±0.20, 14.04±0.20, 17.30±0.20, 18.06±0.20, 20.30±0.20, 21.42±0.20, 23.48±0.20, 25.54±0.20, 26.96±0.20, 29.30±0.20, and 30.72±0.20. In particular, in this aspect, Form I is characterized by an x-ray powder diffraction pattern having three or more diffraction peaks, including four or more diffraction peaks, at 2θ values selected from 6.92±0.20, 10.24±0.20, 13.46±0.20, 15.34±0.20, 18.06±0.20, and 21.42±0.20. Crystalline Form I is further characterized by an x-ray powder diffraction pattern having diffraction peaks, at 2θ values of 6.92±0.20, 10.24±0.20, 13.46±0.20, 15.34±0.20, 18.06±0.20, and 21.42±0.20.

As is well known in the field of powder x-ray diffraction, peak positions of XRPD spectra are relatively less sensitive to experimental details, such as details of sample preparation and instrument geometry, than are the relative peak heights. Thus, in one aspect, Form I of crystalline compound 1 is characterized by an x-ray powder diffraction pattern in which the peak positions are substantially in accordance with those shown in FIG. 1.

The structure of crystalline Form I has been further characterized by single crystal x-ray diffraction analysis, providing the following lattice parameters: unit cell is orthorhombic with dimensions a=7.546 Å, b=17.003 Å, c=20.628 Å, cell volume (V) of 2646.7 Å$^3$; calculated density is 1.151 g/cm$^3$; space group is P2$_1$2$_1$2$_1$. The resulting molecular structure confirms the asymmetric unit cell does not contain water or other solvent molecules and is consistent with the stereochemistry as depicted above. The C—O bond distances of the carboxylic group as well as the bond lengths and bond angles around the amine nitrogen are consistent with compound 1 in crystalline Form I being a zwitterionic molecule in which a proton has been transferred from the carboxylic acid to the amine nitrogen as represented schematically below:

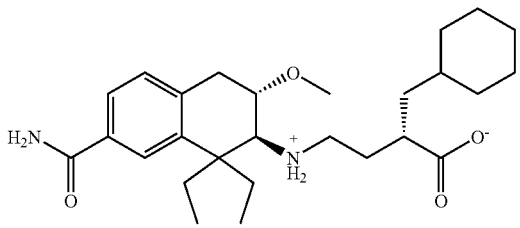

X-ray powder diffraction peaks predicted from the derived atomic positions are in excellent agreement with the observed XRPD pattern.

In another aspect, crystalline Form I is characterized by its behavior when exposed to high temperature. As demonstrated in FIG. 2, the differential scanning calorimetry (DSC) trace exhibits a peak in endothermic heat flow, identified as a melt transition, in the range of about 162° C. to about 170° C., including between about 164° C. and about 168° C. The thermal gravimetric analysis (TGA) trace shows no significant weight loss at temperatures below the melting point and a step profile consistent with a loss of one mole of water per mole of compound 1 at a temperature around the melting point. The release of water can be attributed to a chemical degradation reaction.

Figure 3:
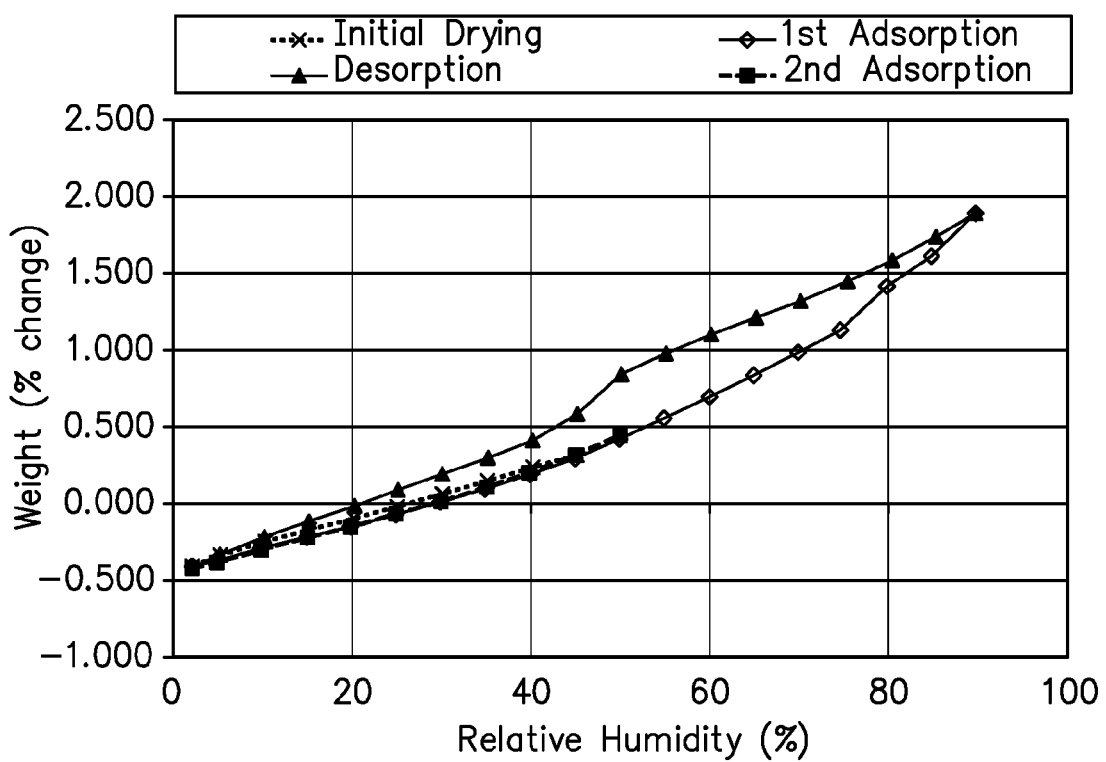
FIG. 3 shows a dynamic moisture sorption (DMS) trace of crystalline Form I (S)-4-((2S,3S)-7-carbamoyl-1,1-diethyl-3-methoxy-1,2,3,4-tetrahydronaphthalen-2-ylamino)-2-cyclohexylmethyl-butyric acid of the invention.

Crystalline Form I has been demonstrated to have a reversible sorption/desorption profile with a small propensity for hygroscopicity. Form I demonstrated less than about 2.5% weight gain in the humidity range of 2% to 90% relative humidity at room temperature, as shown in FIG. 3. In particular, Form I demonstrated less than about 1% weight gain in the range of 40% to 75% relative humidity, the humidity range at which oral formulations are typically manufactured.

In another aspect, the invention provides compound 1 in crystalline Form II. Crystalline Form II is identified by the XRPD pattern of FIG. 4 and the DSC profile of FIG. 5. In one aspect, crystalline Form II is characterized by an x-ray powder diffraction (XRPD) pattern having diffraction peaks at 2θ values of 9.05±0.20 and 16.52±0.20, and having two or more diffraction peaks, including three or more and four or more diffraction peaks, at 2θ values selected from 9.80±0.20, 12.44±0.20, 12.92±0.20, 14.21±0.20, 15.62±0.20, 17.27±0.20, 19.04±0.20, 19.85±0.20, 21.29±0.20, 22.43±0.20, 23.48±0.20, 23.99±0.20, and 26.09±0.20. In particular, in this aspect, Form II is characterized by an x-ray powder diffraction pattern having two or more diffraction peaks, including three or more and four or more diffraction peaks, at 2θ values selected from 9.05±0.20, 9.80±0.20, 12.44±0.20, 12.92±0.20, 16.52±0.20, 23.99±0.20, and 26.09±0.20. Form II is still further characterized by an x-ray powder diffraction pattern having diffraction peaks at 9.05±0.20, 9.80±0.20, 12.44±0.20, 12.92±0.20, 16.52±0.20, 23.99±0.20, and 26.09±0.20. In yet another aspect, crystalline Form II is characterized by an x-ray powder diffraction pattern in which the peak positions are substantially in accordance with those shown in FIG. 4.

Figure 5:
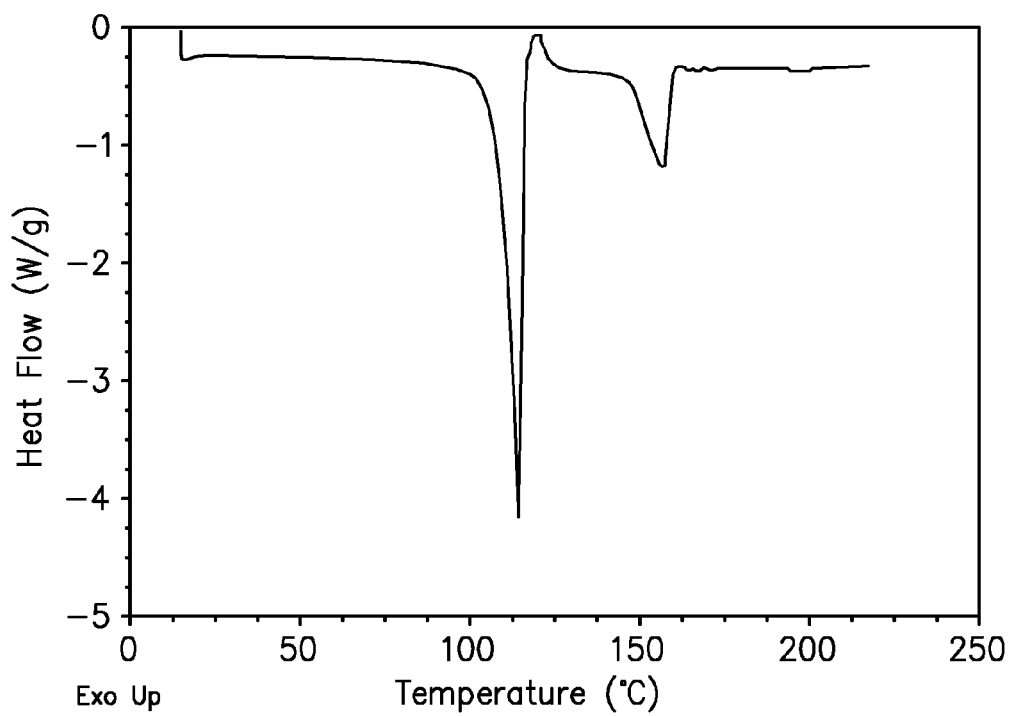
FIG. 5 shows a differential scanning calorimetry (DSC) trace of crystalline Form II (S)-4-((2S,3S)-7-carbamoyl-1,1-diethyl-3-methoxy-1,2,3,4-tetrahydronaphthalen-2-ylamino)-2-cyclohexylmethyl-butyric acid of the invention.

The thermal behavior exhibited in FIG. 5 is consistent with the identification of crystalline Form II as a metastable form which undergoes a transformation at a temperature around 114° C. to 115° C. and has a melting point accompanied by chemical degradation at a temperature around 157° C.

In still another aspect, the invention provides a crystalline hydrochloride salt of compound 1.

In one aspect, a crystalline hydrochloride salt of the present invention is characterized by an x-ray powder diffraction (XRPD) pattern having two or more diffraction peaks, including three or more and four or more diffraction peaks, at 2θ values selected from 6.80±0.20, 9.80±0.20, 12.71±0.20, 13.31±0.20, 15.14±0.20, 19.97±0.20, 21.44±0.20, 22.64±0.20, 23.27±0.20, 24.44±0.20, and 25.37±0.20. In another aspect, a crystalline hydrochloride salt of compound 1 is characterized by an x-ray powder diffraction pattern in which the peak positions are substantially in accordance with those shown in FIG. 6.

Figure 7:
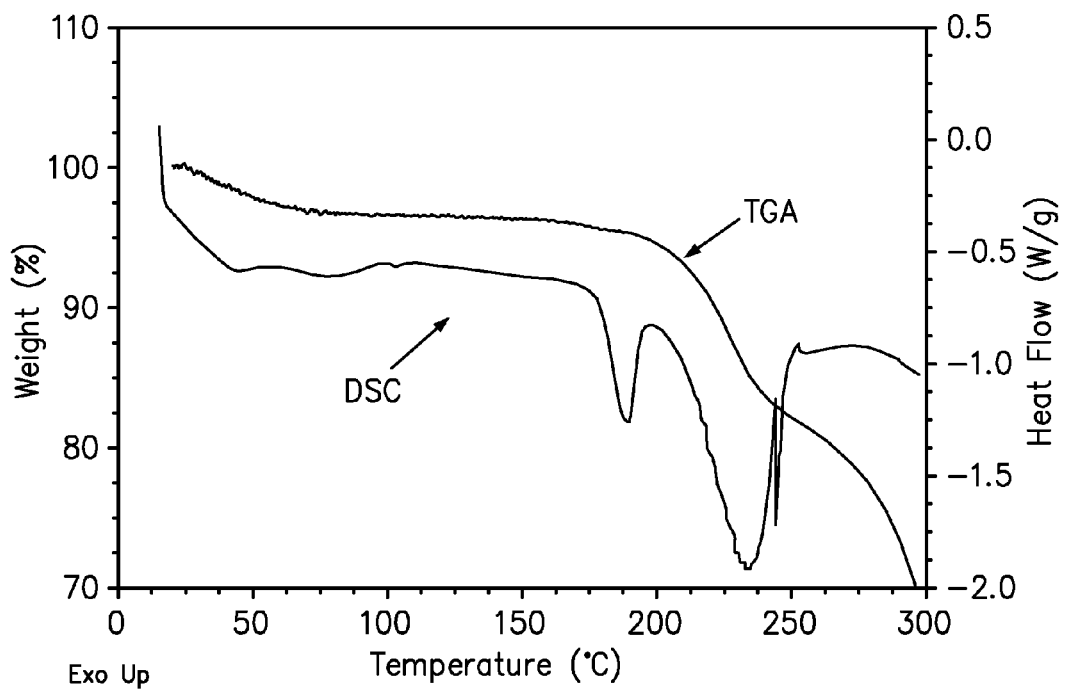
FIG. 7 shows a differential scanning calorimetry (DSC) trace (right side vertical axis) and a thermal gravimetric analysis (TGA) trace (left side vertical axis) of a crystalline hydrochloride salt of (S)-4-((2S,3S)-7-carbamoyl-1,1-diethyl-3-methoxy-1,2,3,4-tetrahydronaphthalen-2-ylamino)-2-cyclohexylmethyl-butyric acid of the invention.

The crystalline hydrochloride salt is also characterized by its differential scanning calorimetry (DSC) trace which exhibits a first peak in endothermic heat flow in the range of about 185° C. to about 193° C., identified as a melting transition, and a second peak in the range of about 220° C. to about 140° C. that is understood to conform to a degradation event, as illustrated in FIG. 7. Samples of the crystalline hydrochloride salt prepared in Examples 8, 9, and 10 retained their appearance and flowability when exposed to relative humidity in the range of about 2% relative humidity to about 90% relative humidity at room temperature.

These properties of the crystalline forms of this invention are further illustrated in the Examples below.

Synthetic Procedures and Intermediates

Compound 1, (S)-4-((2S,3S)-7-carbamoyl-1,1-diethyl-3-methoxy-1,2,3,4-tetrahydronaphthalen-2-ylamino)-2-cyclohexylmethyl-butyric acid can be prepared from readily available starting materials in solid amorphous form using the procedures described in the Examples below, or using the procedures described in the commonly-assigned U.S. applications listed in the Background section of this application.

In one method of preparation, crystalline Form I of the invention is prepared by dissolving amorphous compound 1 in a polar diluent to form a crystallization process mixture, and holding the process mixture for between about 12 hours and about 4 days. Typically the crystallization process is conducted at about ambient temperature. Suitable diluents include methanol, isopropanol, 1-propanol, and acetonitrile, and mixtures of one or more of the foregoing with water. Exemplary diluent systems include a mixture of acetonitrile, methanol and water, for example, about 69% acetonitrile, about 21% methanol and about 10% water; a mixture of 1-propanol, acetonitrile, and water, in particular about 95% to about 97% (2:1 1-propanol:acetonitrile) and about 5% to about 3% water; a mixture of methanol and water, for example, about 90% methanol and about 10% water; and a mixture of acetonitrile and water, for example about 84% acetonitrile and about 16% water. Compound 1 is typically present in the process mixture at a concentration of between about 150 mg/mL and about 700 mg/mL.

When water is not present in the diluent system, it is useful to hold the process mixture for a time period at the upper end of the stated range (See, Example 4 below, where crystallization was allowed to proceed over 4 days.) A useful process, therefore, for preparing crystalline Form I comprises dissolving compound 1 in a diluent comprising a polar diluent and between about 3% and about 20% water to form a process mixture; holding the process mixture for at least about 12 hours; and recovering the resulting crystals.

Upon completion of the reaction, crystalline Form I is isolated from the process mixture by any conventional means, such as filtration, concentration, centrifugation, and the like.

In another method of preparation, crystalline Form I is advantageously prepared directly from a protected precursor 2 of compound 1, according to the following process:

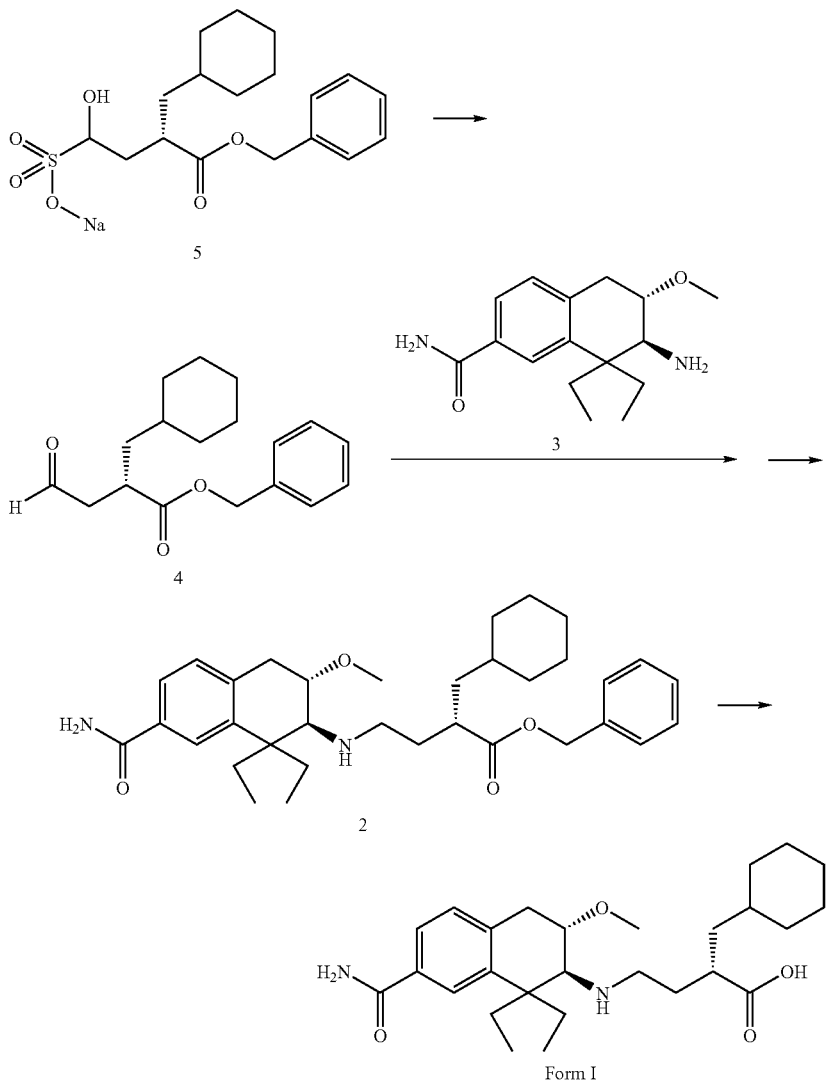

As summarized in Scheme A, benzyl-protected aldehyde 4 is reacted with aminotetralin intermediate 3 to provide a benzyl-protected precursor 2, which is deprotected to provide compound 1 in crystalline Form I. The aldehyde reagent 4 is conveniently prepared in situ from the corresponding bisulfite adduct 5.

In a typical process, a solution of between about 1 and about 1.5 equivalents of aldehyde 4 in an inert diluent is generated by treating the bisulfite adduct 5 with an equal number of equivalents of sodium hydroxide. The aldehyde 4 is then contacted with aminotetralin 3 and between about 1 and about 3 equivalents of a reducing agent, such as sodium triacetoxyborohydride. Aminotetralin 3 may be provided as an acid salt, typically a hydrochloride salt. The reaction is typically conducted at a temperature between about 0° C. and about 30° C. for between about 2 and about 24 hours or until the reaction is substantially complete. The protected intermediate 2 is conveniently isolated in solid form as a crystalline hydrochloride salt.

Finally, intermediate 2 is debenzylated by catalytic hydrogenolysis, typically using a transition metal catalyst, for example, palladium or platinum, to provide crystalline Form I. When intermediate 2 is provided in salt form, the neutral form of the intermediate is first generated in situ by treatment with base. The reaction is conducted in a diluent chosen to be both compatible with hydrogenolysis and conducive to crystallization. Mixtures comprising water and another polar diluent, such as methanol, isopropanol, 1-propanol, acetonitrile, and/or dimethylformamide, are suitable for this reaction. Mixtures comprising between about 10% and about 20% water, for example, a mixture of acetonitrile and between about 10% and about 20% water, are advantageously used in the debenzylation reaction. The reaction product, crystalline Form I, can be isolated by conventional means, such as filtration.

Accordingly, in a method aspect, among other processes, the invention provides a process for preparing crystalline Form I of compound 1, the process comprising: deprotecting the benzyl-protected intermediate 2 by catalytic hydrogenolysis in the presence of a polar diluent comprising between about 10% and about 20% water to form crystalline Form I.

In an additional method aspect, the invention provides a process for preparing crystalline Form I of compound 1, the process comprising (a) reacting protected aldehyde 4 with aminotetralin 3 to provide protected intermediate 2, and (b) deprotecting the benzyl-protected intermediate 2 by catalytic hydrogenolysis in the presence of a polar diluent comprising between about 10% and about 20% water to form crystalline Form I.

Deprotection of intermediate 2 in a diluent that is compatible with hydrogenolysis but that does not promote crystallization, such as, ethyl acetate, tetrahydrofuran, or methyltetrahydrofuran, results in the preparation of compound 1, albeit not necessarily in crystalline form. In yet another method aspect, the invention provides a process for preparing compound 1, the process comprising (a) reacting protected aldehyde 4 with aminotetralin 3 to provide protected intermediate 2, and (b) deprotecting the benzyl-protected intermediate 2 by catalytic hydrogenolysis to provide compound 1.

Further, in a composition aspect, the invention provides the benzyl-protected aldehyde 4, (S)-2-cyclohexylmethyl-4-oxo-butyric acid benzyl ester, and the bisulfite adduct 5, sodium (S)-3-benzyloxycarbonyl-4-cyclohexyl-1-hydroxy-butane-1-sulfonate useful for preparing compound 1. As described in Preparation 8, the benzyl-protected bisulfite adduct 5 can be prepared from the corresponding methyl ester bisulfite, sodium (S)-4-cyclohexyl-1-hydroxy-3-methoxycarbonyl-butane-1-sulfonate, synthesis of which is described in Preparation 7. Alternatively, bisulfite adduct 5 could be prepared by processes analogous to those of Preparation 7 through analogous benzyl-protected carboxylic acid (5a) and alcohol (5b) intermediates:

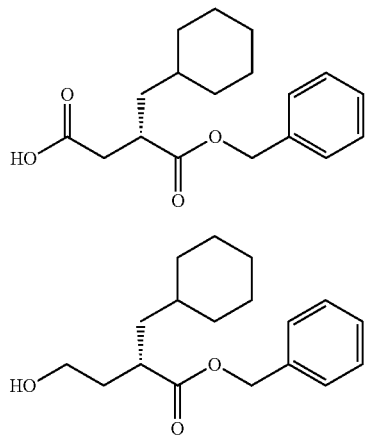

In yet another composition aspect, the invention provides the benzyl-protected precursor 2, (S)-4-((2S,3S)-7-carbamoyl-1,1-diethyl-3-methoxy-1,2,3,4-tetrahydro-naphthalen-2-ylamino)-2-cyclohexylmethyl-butyric acid benzyl ester and the hydrochloride salt, thereof. The crystalline hydrochloride salt of compound 2 is characterized by the XRPD pattern of FIG. 8 and the DSC profile of FIG. 9 which exhibits a peak in endothermic heat flow, consistent with a melting point, at a temperature between about 205° C. and about 210° C. Pharmaceutical intermediates in crystalline form are desirable both due to the typical purification that results from crystallization and due to the expected greater stability on storage as compared with non-crystalline material.

As described in the Examples below, crystalline Form II is prepared by dissolving amorphous compound 1 in a polar diluent comprising alcohol, for example, isopropanol, or isopropanol and acetonitrile at a concentration between about 150 mg/mL and about 700 mg/mL to form a crystallization process mixture, and holding the process mixture for less than about a day. Optionally an anti-solvent, for example 1:1 acetonitrile:ethyl acetate can be added to the process mixture before the holding period to promote crystallization from solution.

The crystalline hydrochloride salt of the present invention is advantageously prepared from the amorphous hydrochloride salt of compound 1. The amorphous salt of compound 1 is dispersed in a moderately polar solvent such as ethyl acetate or diethylene glycol dimethyl ether, at a concentration between about 20 mg/mL and about 350 mg/mL, optionally with heating followed by slow cooling, and then held for a period of between about 3 days and about 12 days. The resulting crystals can be isolated conventionally.

Pharmaceutical Compositions

The crystalline solid forms of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a crystalline solid form of compound 1 or a crystalline hydrochloride salt of compound 1. Optionally, such pharmaceutical compositions may contain other therapeutic and/or formulating agents if desired. When discussing compositions, it is understood the term "solid form of the invention" includes the crystalline Forms I and II of compound 1 as well as a crystalline hydrochloride salt of compound 1.

The pharmaceutical compositions of the invention typically contain a therapeutically effective amount of the active agent. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The solid forms of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The solid forms of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the solid forms of this invention may be administered in combination with one or more other therapeutic agents. In this embodiment, a solid form of this invention is either physically mixed with the other therapeutic agent to form a composition containing both agents; or each agent is present in separate and distinct compositions which are administered to the patient simultaneously or sequentially.

For example, a solid form of the invention can be combined with second therapeutic agent using conventional procedures and equipment to form a composition comprising a compound 1 and a second therapeutic agent. Additionally, the therapeutic agents may be combined with a pharmaceutically acceptable carrier to form a pharmaceutical composition comprising a salt of the invention, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or may be packaged together as a kit. The two therapeutic agents in the kit may be administered by the same route of administration or by different routes of administration.

Any therapeutic agent compatible with the present active agent may be used as the second therapeutic agent. In particular, prokinetic agents acting via mechanisms other than mu opioid receptor antagonism may be used in combination with the present compounds. For example, 5-HT$_4$ receptor agonists, such as tegaserod, renzapride, mosapride, prucalopride, 1-isopropyl-1H-indazole-3-carboxylic acid {(1S,3R,5R)-8-[2-(4-acetylpiperazin-1-yl)ethyl]-8-azabicyclo [3.2.1] oct-3-yl}amide, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo [3.2.1]oct-3-yl}amide, or 4-(4-{[(2-isopropyl-1H-benzoimidazole-4-carbonyl)amino]methyl}-piperidin-1-ylmethyl)piperidine-1-carboxylic acid methyl ester may be used as the second therapeutic agent.

Additional useful prokinetic agents include, but are not limited to, 5-HT$_3$ receptor agonists (e.g. pumosetrag), 5-HT$_{1A}$ receptor antagonists (e.g. AGI 001), alpha-2-delta ligands (e.g. PD-217014), chloride channel openers (e.g. lubiprostone), dopamine antagonists (e.g. itopride, metaclopramide, domperidone), GABA-B agonists (e.g. baclofen, AGI 006), kappa opioid agonists (e.g. asimadoline), muscarinic M$_1$ and M$_2$ antagonists (e.g. acotiamide), motilin agonists (e.g. mitemcinal), guanylate cyclase activators (e.g. MD-1100) and ghrelin agonists (e.g. Tzp 101, RC 1139).

In addition, the solid forms of the invention can be combined with opioid therapeutic agents. Such opioid agents include, but are not limited to, morphine, pethidine, codeine, dihydrocodeine, oxycontin, oxycodone, hydrocodone, sufentanil, fentanyl, remifentanil, buprenorphine, methadone, and heroin.

Numerous additional examples of such therapeutic agents are known in the art and any such known therapeutic agents may be employed in combination with the compounds of this invention. Secondary agent(s), when included, are present in a therapeutically effective amount, i.e. in any amount that produces a therapeutically beneficial effect when co-administered with a compound of the invention. Suitable doses for the other therapeutic agents administered in combination with a compound of the invention are typically in the range of about 0.05 µg/day to about 100 mg/day.

Accordingly, the pharmaceutical compositions of the invention optionally include a second therapeutic agent as described above.

The following examples illustrate representative pharmaceutical compositions of the present invention:

FORMULATION EXAMPLE A

Hard Gelatin Capsules for Oral Administration

A solid form of the invention (50 g), spray-dried lactose (200 g) and magnesium stearate (10 g) are thoroughly blended. The resulting composition is loaded into a hard gelatin capsule (260 mg of composition per capsule).

FORMULATION EXAMPLE B

Hard Gelatin Capsules for Oral Administration

A solid form of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

FORMULATION EXAMPLE C

Gelatin Capsules for Oral Administration

A solid form of the invention (10 mg), polyoxyethylene sorbitan monooleate (50 mg), and starch powder (250 mg) are thoroughly blended and then loaded into a gelatin capsule (310 mg of composition per capsule).

FORMULATION EXAMPLE D

Tablets for Oral Administration

A solid form of the invention (5 mg), starch (50 mg), and microcrystalline cellulose (35 mg) are passed through a No. 45 mesh U.S. sieve and mixed thoroughly. A solution of polyvinylpyrrolidone (10 wt % in water, 4 mg) is mixed with the resulting powders, and this mixture is then passed through a No. 14 mesh U.S. sieve. The granules so produced are dried at 50-60° C. and passed through a No. 18 mesh U.S. sieve. Sodium carboxymethyl starch (4.5 mg), magnesium stearate (0.5 mg) and talc (1 mg), which have previously been passed through a No. 60 mesh U.S. sieve, are then added to the granules. After mixing, the mixture is compressed on a tablet machine to afford a tablet weighing 100 mg.

FORMULATION EXAMPLE E

Tablets for Oral Administration

A solid form of the invention (25 mg), microcrystalline cellulose (400 mg), fumed silicon dioxide (10 mg), and stearic acid (5 mg) are thoroughly blended and then compressed to form tablets (440 mg of composition per tablet).

FORMULATION EXAMPLE F

Single-scored Tablets For Oral Administration

A solid form of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

FORMULATION EXAMPLE G

Suspension for Oral Administration

The following ingredients are thoroughly mixed to form a suspension for oral administration containing 100 mg of active ingredient per 10 mL of suspension:

| Ingredients | Amount | |
|---|---|---|
| Solid form of the invention | 0.1 | g |
| Fumaric acid | 0.5 | g |
| Sodium chloride | 2.0 | g |
| Methyl paraben | 0.15 | g |
| Propyl paraben | 0.05 | g |
| Granulated sugar | 25.5 | g |
| Sorbitol (70% solution) | 12.85 | g |
| Veegum k (Vanderbilt Co.) | 1.0 | g |
| Flavoring | 0.035 | mL |
| Colorings | 0.5 | mg |
| Distilled water | q.s. to 100 | mL |

FORMULATION EXAMPLE H

Dry Powder Composition

A micronized solid form of the invention (1 mg) is blended with lactose (25 mg) and then loaded into a gelatin inhalation cartridge. The contents of the cartridge are administered using a powder inhaler.

FORMULATION EXAMPLE J

Injectable Formulation

A solid form of the invention (0.1 g) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

It will be understood that any solid form of the invention, (i.e. crystalline Form I or Form II, or crystalline hydrochloride salt) that is suitable for the particular mode of administration, can be used in the pharmaceutical compositions discussed above.

Utility

The present active agent, (S)-4-((2S,3S)-7-carbamoyl-1,1-diethyl-3-methoxy-1,2,3,4-tetrahydronaphthalen-2-ylamino)-2-cyclohexylmethyl-butyric acid, is an antagonist at the mu opioid receptor and therefore the crystalline solid forms of the invention are expected to be useful for treating medical conditions mediated by mu opioid receptors or associated with mu opioid receptor activity, i.e. medical conditions which are ameliorated by treatment with a mu opioid receptor antagonist. In particular, the solid forms of the invention are expected to be useful for treating adverse effects associated with use of opioid analgesics, i.e. symptoms such as constipation, decreased gastric emptying, abdominal pain, bloating, nausea, and gastroesophageal reflux, termed collectively opioid-induced bowel dysfunction. The present solid forms are also expected to be useful for treating post-operative ileus, a disorder of reduced motility of the gastrointestinal tract that occurs after abdominal or other surgery. In addition, it has been suggested that mu opioid receptor antagonist compounds, such as compound 1 may be used for reversing opioid-induced nausea and vomiting.

Since compound 1 has been shown to increase motility of the gastrointestinal (GI) tract in animal models, the solid forms of the invention are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a solid form of the invention.

When used to treat disorders of reduced motility of the GI tract or other conditions mediated by mu opioid receptors, the solid forms of the invention will typically be administered orally in a single daily dose or in multiple doses per day, although other forms of administration may be used. For example, particularly when used to treat post-operative ileus, the solid forms of the invention may be administered parenterally. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by mu opioid receptors will range from about 0.0007 to about 20 mg/kg/day of active agent, including from about 0.0007 to about 1.4 mg/kg/day. For an average 70 kg human, this would amount to from about 0.05 to about 100 mg per day of active agent.

In one aspect of the invention, the solid forms of the invention are used to treat opioid-induced bowel dysfunction. When used to treat opioid-induced bowel dysfunction, the solid forms of the invention will typically be administered orally in a single daily dose or in multiple doses per day. Preferably, the dose for treating opioid-induced bowel dysfunction will range from about 0.05 to about 100 mg per day.

In another aspect of the invention, the solid forms of the invention are used to treat post-operative ileus. When used to treat post-operative ileus, the solid forms of the invention will typically be administered orally or intravenously in a single daily dose or in multiple doses per day. Preferably, the dose for treating post-operative ileus will range from about 0.05 to about 100 mg per day.

The invention also provides a method of treating a mammal having a disease or condition associated with mu opioid receptor activity, the method comprising administering to the mammal a therapeutically effective amount of a solid form of the invention or of a pharmaceutical composition comprising a solid form of the invention.

The present active agent is optionally administered in combination with another therapeutic agent or agents, in particular, in combination with prokinetic agents acting via non-mu opioid mechanisms. Accordingly, in another aspect, the methods and compositions of the invention further comprise a therapeutically effective amount of another prokinetic agent.

As described above, solid forms of the invention are mu opioid receptor antagonists. The invention further provides, therefore, a method of antagonizing a mu opioid receptor in a mammal, the method comprising administering a solid form of the invention to the mammal.

Among other properties, the present active agent has been found to exhibit potent binding to mu opioid receptors and little or no agonism in mu receptor functional assays. Therefore, the solid forms of the invention are potent mu opioid receptor antagonists. Further, the active agent has demonstrated predominantly peripheral activity as compared with central nervous system activity in animal models. Therefore, the solid forms of the invention can be expected to reverse opioid-induced reductions in GI motility without interfering with the beneficial central effects of analgesia. These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

| | |
|---|---|
| DCM = | dichloromethane |
| DMF = | N,N-dimethylformamide |
| MeOH = | methanol |
| MeTHF = | 2-methyltetrahydrofuran |
| MTBE = | tert-butyl methyl ether |
| psi = | pounds per square inch |
| RT = | room temperature |

Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), high performance liquid chromatography (HPLC), and mass spectrometry. Reaction mixtures were worked up as described specifically in each reaction; commonly they were purified by extraction and other purification methods such as temperature-, and solvent-dependent precipitation. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1200 LC/MSD instrument. Water content was determined by Karl-Fischer titration using a Brinkmann (Westbury, N.Y.) Metrohm Karl Fischer Model 813 coulometer. Purity was determined by HPLC using the following conditions:

| | |
|---|---|
| Column: | Zorbax SB-Aq, 5 µm. 4.6 × 250 mm |
| Column temperature: | 40° C. |
| Flow rate: | 1.0 mL/min |
| Mobile Phases: | A = Water/ACN (98:2) + 0.1 % TFA |
| | B = Water/ACN (10:90) + 0.1 % TFA, |
| Injection volume: | 10 µL |
| Detector wavelength: | 214 nm |

Compounds were dissolved in Water/ACN (50:50) at about 1 mg/mL and analyzed using the following gradient over 20 min (time (min)/% B): 0/10, 2.5/20, 9/75, 15/90, 17/90, 18/10, 20/10.

Preparation 1: 7,7-diethyl-5-hydroxy-1a,2,7,7a-tetrahydro-1-aza-cyclopropa[b]naphthalene-1-carboxylic acid tert-butyl ester a. 7-Amino-6-bromo-8,8-diethyl-5,6,7,8-tetrahydronaphthalen-2-ol hydrobromide To a flask was added 7,7-diethyl-5-methoxy-1a,2,7,7a-tetrahydro-1H-1-aza-cyclopropa[b]naphthalene (268 g, 1.16 mol) and hydrogen bromide (1.97 L, 17.38 mol), followed by tetra-N-butylammonium bromide (38 g, 0.12 mol). The reaction mixture was heated at 100° C. overnight with stirring, cooled to room temperature and then poured into stirred ethyl acetate (2.5 L). The product was isolated by filtration, the filter cake was washed with ethyl acetate (2×200 mL) and dried to yield crude product (370 g) as a purplish solid. The crude product was suspended in ethanol (1.50 L) then heated at 80° C. for 30 min. The resulting slurry was cooled to room temperature over 1 h, and filtered. The flask and filter cake with were washed with ethanol (2×100 mL) and then with ethyl acetate (100 mL) and dried overnight to yield the title compound (275 g, ~96% purity).

b. 7,7-Diethyl-5-hydroxy-1a,2,7,7a-tetrahydro-1-aza-cyclopropa[b]naphthalene-1-carboxylic acid tent-butyl ester To a slurry of 7-amino-6-bromo-8,8-diethyl-5,6,7,8-tetrahydronaphthalen-2-ol hydrobromide (20.0 g, 52.8 mmol) and ethyl acetate (200 mL) was added 1.0 M sodium hydroxide in water (106 mL). The reaction mixture was stirred at 25° C. for 2 h, di-tert-butyldicarbonate (15 g, 68 mmol) in ethyl acetate (5 mL) was added and the reaction mixture was stirred at room temperature for 2 h. Following removal of two-thirds of the ethyl acetate (135 mL), heptane (135 mL) was added and the resulting slurry was stirred at room temperature over 30 min and then at 5° C. overnight. The slurry was filtered, and the filter cake was rinsed with water (100 mL), rinsed with heptane (50 mL), and dried under vacuum to give the title compound (14.3 g).

Preparation 2: trans-(7-Cyano-1,1-diethyl-3-methoxy-1,2,3,4-tetrahydro-naphthalen-2-yl)-carbamic acid tert-butyl ester* a. trans-(1,1-Diethyl-7-hydroxy-3-methoxy-1,2,3,4-tetrahydronaphthalen-2-yl)-carbamic acid tert-butyl ester To a slurry of 7,7-diethyl-5-hydroxy-1a,2,7,7a-tetrahydro-1-aza-cyclopropa[b]naphthalene-1-carboxylic acid tert-butyl ester (170.0 g, 535.6 mmol) and methanol (1700 mL) was added pyridiniump-toluenesulfonate (13.4 g, 53.6 mmol) and the reaction mixture was stirred at 40° C. for 4 h. The volume was reduced by rotary evaporation to ~300 mL resulting in a thick white slurry. The product was isolated by filtration; the filter cake was washed with cold methanol (50 mL) and dried in air for 3 h to yield the title compound (150 g). The filtrate was reduced to ~50 mL and stirred at 0° C. for 2 h, filtered, and dried to yield additional product (25 g).

b. trans-Trifluoro-methanesulfonic acid 7-tert-butoxycarbonylamino-8,8-diethyl-6-methoxy-5,6,7,8-tetrahydronaphthalen-2-yl ester A mixture of trans-(1,1-diethyl-7-hydroxy-3-methoxy-1,2,3,4-tetrahydro-naphthalen-2-yl)-carbamic acid tert-butyl ester (195.0 g, 0.558 mol), triethylamine (160 mL, 1.1 mol) and ethyl acetate (2000 mL) was stirred at room temperature for 15 min and cooled to 0° C. followed by slow addition of trifluoro-methanesulfonyl chloride (150 g, 0.89 mol) keeping the internal temperature below 4° C. The resulting slurry was stirred at 0° C. for 1 h. Additional triethylamine (16 mL) followed by additional trifluoromethanesulfonyl chloride (15.0 g) was added slowly maintaining a temperature below 5° C. The reaction mixture was stirred at room temperature for an additional hour. Diluted brine (1.0 L) was added and the reaction mixture was stirred for 10 min at room temperature. The layers were separated; the organic layer was washed with diluted NaHCO$_3$ (1.0 L) and then concentrated to ~350 mL by rotary evaporation at 28° C. and stirred at room temperature for 30 min. Heptane (700 mL) was added and the resulting slurry was stirred at room temperature for 30 min, cooled to 4° C. and stirred for 1 h. The solids were filtered, washed with heptane, and then dried under vacuum to yield the title compound (193.0 g, >97% purity). The filtrate was concentrated, slurried in an isopropyl acetate and heptane mixture (1:3, 60 mL) over 30 min, filtered and dried to yield additional product (45.0 g, >97% purity).

c. trans-(7-Cyano-1,1-diethyl-3-methoxy-1,2,3,4-tetrahydronaphthalen-2-yl)-carbamic acid tert-butyl ester Trifluoro-methanesulfonic acid 7-tert-butoxycarbonylamino-8,8-diethyl-6-methoxy-5,6,7,8-tetrahydro-naphthalen-2-yl ester (236.6 g, 0.49 mol) was dissolved in N,N-dimethylformamide (851 mL, 10.99 mol) and water (23.8 mL, 1.32 mol) at room temperature. The solution was purged with nitrogen for 5 min, and then connected to house vacuum for 5 min. Nitrogen purging and exposure to vacuum was repeated twice. To the reaction mixture was added zinc cyanide (34.2 g, 0.29 mol), tris(dibenzylideneacetone)dipalladium(0) (4.4 g, 4.8 mmol) and 1,1'-bis(diphenylphosphino) ferrocene (5.4 g, 9.7 mmol) with stirring. The reaction mixture was purged with nitrogen for 5 min, heated under nitrogen at 110° C. for 1 h, cooled to room temperature and then filtered through celite. The filtered reaction mixture was added slowly to water (3 L), cooled to 0° C. with stirring, stirred for 30 min at 0° C., and then filtered. The filter cake was washed with water (500 mL) and dried in air for 2 h, slurried in ethanol (1 L) with stirring over 1 h, and then filtered to give the title compound (165.0 g, >96% purity). The filtrate was dried (21.6 g) and dissolved in ethanol (110 mL) with stirring over 1 h, and the resulting slurry was filtered and dried under vacuum to give additional product (10.2 g, >98% purity).

*In this and the following examples, the prefix trans refers to a mixture of the (2S),(2S) diastereomer and the (2R),(2R) diastereomer.

Preparation 3: trans-(7-Carbamoyl-1,1-diethyl-3-methoxy-1,2,3,4-tetrahydronaphthalen-2-yl)-carbamic acid tert-butyl ester A slurry of the product of Preparation 2 (160.0 g, 446.3 mmol) and methanol (3.3 L) was heated at 55° C. for 15 min, sodium perborate monohydrate (280 g, 2800 mmol) and water (330 mL) was added and the reaction mixture was heated at 55° C. overnight. Additional sodium perborate monohydrate (90 g) was added and the reaction mixture was heated at 55° C. overnight, then cooled to room temperature, and the inorganic solids were filtered off. The filtrate was transferred to a 5 L flask and most of the solvent was removed by rotary evaporation. To the resulting slurry was added water (1.1 L) and ethyl acetate (450 mL) and the reaction mixture was stirred at room temperature for 20 min. The reaction mixture was filtered and the filter cake was washed with water (200 mL) and then ethyl acetate (200 mL) and dried to yield the title compound (123 g, ~95% purity). The filtrate was concentrated to dryness and dried under vacuum to yield additional product (18 g, 65% purity).

Preparation 4: trans-7-Amino-8,8-diethyl-6-methoxy-5,6,7,8-tetrahydro-naphthalene-2-carboxylic acid amide Acetyl chloride (278.8 mL, 3920 mmol) was added dropwise to ethanol (382 mL, 6530 mmol) at −5° C. over 2 h keeping the internal temperature below 20° C. The resulting solution was added portion wise over 15 min, keeping the internal temperature below 30° C., to a slurry of trans-(7-carbamoyl-1,1-diethyl-3-methoxy-1,2,3,4-tetrahydro-naphthalen-2-yl)-carbamic acid tert-butyl ester (123.0 g, 327 mmol) and ethanol (500 mL) that had been cooled to 10° C. The reaction mixture was stirred at room temperature for 2 h, and concentrated to ~200 mL by rotary evaporation. Ethyl acetate (200 mL) was added and the resulting slurry was stirred at 0° C. for 30 min, filtered and dried to yield the hydrochloride salt of the title compound (102 g, >98% purity) as a white solid.

Preparation 5: Carbonic acid 4-nitro-phenyl ester (R)-1-phenyl-ethyl ester

A mixture of (R)-1-phenyl-ethanol (60.6 g, 0.496 mol), pyridine (42.5 mL, 0.526 mol) and 2-methyl-tetrahydrofuran (600 mL) was cooled to 0° C. and p-nitrophenyl chloroformate (100 g, 0.496 mol) was added over 15 min keeping the internal temperature below 5° C. The reaction mixture was warmed to room temperature and stirred for 2 h. To the reaction mixture was added 1.0 M HCl in water (300 mL). Layers were separated. The organic layer was washed with 1N HCl (300 mL) and brine (300 mL), filtered, concentrated to dryness by rotary evaporation, and dried under vacuum to give the title compound (140 g) as a clear yellow oil.

Preparation 6: (6S,7S)-7-Amino-8,8-diethyl-6-methoxy-5,6,7,8-tetrahydro-naphthalene-2-carboxylic acid amide a. ((2S,3S)-7-Carbamoyl-1,1-diethyl-3-methoxy-1,2,3,4-tetrahydro-naphthalen-2-yl)-carbamic acid (R)-1-phenyl-ethyl ester A mixture of carbonic acid 4-nitro-phenyl ester (R)-1-phenyl-ethyl ester (102 g, 357 mmol), N,N-dimethylformamide (200 mL) and triethylamine (32.7 mL, 235 mmol) was stirred at room temperature overnight. To the reaction mixture was added trans-7-amino-8,8-diethyl-6-methoxy-5,6,7,8-tetrahydro-naphthalene-2-carboxylic acid amide hydrochloride (100 g, 320 mmol), N,N-dimethylformamide (320 mL) and triethylamine (98.0 mL, 703 mmol). The reaction mixture was heated at 85° C. for 5 h and then stirred at room temperature overnight. Approximately 90% of the DMF was removed by distillation at 70° C. and the resulting thick oil was cooled to room temperature and then partitioned between ethyl acetate (1.5 L) and diluted brine (500 mL). The organic layer was washed with 1M NaOH (3×500 mL) and dried with $Na_2SO_4$. Most of the solvent was removed by rotary evaporation, 3 volumes ethyl acetate were added and resulting slurry was stirred at room temperature for 30 min, filtered and dried to give the title compound (48 g, >99% chemical and optical purity).

The filtrate was washed with 1M NaOH (200 mL) and then with diluted brine (2×200 mL). Most of the solvent was removed by rotary evaporation yielding a thick oil to which ethyl acetate (100 mL) was added. A pinch of seeds of the title compound was added and the reaction mixture was refrigerated at 0° C. after stirring for ~30 min. The resulting thin slurry was stirred for 5 min and filtered; flask and filter cake were washed with ethyl acetate (2×15 mL) to yield additional title compound (4.1 g, 97% chemical and >99% optical purity, 38% combined yield).

b. (6S,7S)-7-Amino-8,8-diethyl-6-methoxy-5,6,7,8-tetrahydronaphthalene-2-carboxylic acid amide Acetyl chloride (193 mL, 2710 mmol) was added dropwise to ethanol (260 mL, 4500 mmol) at −5° C. over 40 min keeping the internal temperature below 30° C. The resulting solution was added over 5 min, at 10° C., to a mixture of ((2S,3S)-7-carbamoyl-1,1-diethyl-3-methoxy-1,2,3,4-tetrahydro-naphthalen-2-yl)-carbamic acid (R)-1-phenyl-ethyl ester (49.0 g, 115 mmol) and ethanol (200 mL). The reaction mixture was stirred at room temperature overnight, and concentrated to ~100 mL by rotary evaporation. Ethyl acetate (100 mL) was added and the resulting slurry was stirred at 0° C. for 30 min and filtered. The filter cake was washed with ethyl acetate and dried to yield the hydrochloride salt of the title compound (30 g, >99% purity). The volume of the filtrate was reduced almost to dryness. Isopropyl alcohol (20 mL) was added and the resulting thick slurry was stirred for 30 min and filtered. The filter cake was washed with ethyl acetate (2×20 mL) and dried under vacuum overnight to yield additional title compound (5.5 g, >97% purity). $^1$H NMR (DMSO-$d_6$): δ (ppm) 0.49 (t, 3H), 0.63 (t, 3H), 1.62 (q, 2H), 1.89 (m, 1H), 2.09 (m, 1H), 2.60 (dd, 1H), 3.22 (m, 1H), 3.41 (s, 3H), 3.50 (dd, 1H), 3.82 (q, 1H), 7.19 (d, 1H), 7.31 (br, 1H), 7.70 (d, 1H), 7.71 (s, 1H), 7.98 (br, 1H), 8.15 (br, 3H).

Preparation 7: Sodium (S)-4-cyclohexyl-1-hydroxy-3-methoxycarbonyl-butane-1-sulfonate a: (S)-2-Cyclohexylmethyl-4-hydroxy-butyric acid methyl ester

A mixture of (S)-2-cyclohexylmethyl-succinic acid 1-methyl ester (60.0 g, 263 mmol) and tetrahydrofuran (600 mL) was stirred at room temperature and then cooled to −5° C. over 30 min. To the reaction mixture was added 1.0 M borane in tetrahydrofuran (520 mL) dropwise over 45 min, keeping the internal temperature below 0° C. To the reaction mixture was added MeOH (100 mL) dropwise to quench the reaction. The reaction mixture was concentrated to about 100 mL by rotary evaporation. (Trifluoromethyl)benzene (200 mL) was added and volume was reduced to 25 mL by rotary evaporation. (Trifluoromethyl)benzene (100 mL) was added to the resulting thick oil and the volume was reduced to ~25 mL to provide crude title product (56.3 g).

b. Sodium (S)-4-cyclohexyl-1-hydroxy-3-methoxycarbonyl-butane-1-sulfonate

A mixture of (S)-2-cyclohexylmethyl-4-hydroxy-butyric acid methyl ester (44.8 g, 209 mmol) and DCM (310 mL) was cooled to 5° C. with stirring. To the reaction mixture was added a solution of potassium bromide (2.5 g, 21 mmol) and sodium bicarbonate (2.4 g, 29 mmol) in distilled water (130 mL), and then 2,2,6,6-tetramethylpiperidin-1-oxyl (TEMPO) (0.33 g, 2.1 mmol), followed by the addition of sodium hypochlorite (140 mL, 210 mmol) at the rate of 130 mL/h keeping the internal temperature in the range of 6-8° C. The reaction mixture was stirred for 15 min and DCM (200 mL) was added. Layers were separated and the organic layer was washed with saturated brine (200 mL), and dried with $Na_2SO_4$.

To the organic layer was added EtOAc (40 mL) followed by the addition of sodium bisulfite (21.8 g, 209 mmol). The reaction solution was concentrated to remove half of the DCM (~175 mL) by rotary evaporation. Water (2 mL) were added to the reaction solution which was stirred at room temperature overnight. The resulting slurry was filtered; the filter cake was dried under vacuum overnight to yield the title compound (61.9 g). $^1$H NMR (DMSO-$d_6$): δ (ppm) 0.78 (m, 2H), 0.95-1.20 (m, 4H), 1.33 (m, 1H), 1.40-1.95 (m, 5H), 2.45-2.65 (m, 1H), 3.21 (m, 2H), 3.45 (s, 3H), 3.6-3.8 (m, 1H), 5.18 (d, 1H).

Preparation 8: Sodium (S)-3-benzyloxycarbonyl-4-cyclohexyl-1-hydroxy-butane-1-sulfonate a. (S)-2-cyclohexylmethyl-4,4-dimethoxy-butyric acid methyl ester

To a slurry of sodium (S)-4-cyclohexyl-1-hydroxy-3-methoxycarbonyl-butane-1-sulfonate (400.0 g, 1.26 mol) and methanol (2 L) was added 4.0 M HCl in 1,4-dioxane (400 mL) and the reaction mixture was stirred for 15 min. Trimethoxymethane (340 mL, 3.11 mol) was added and reaction mixture was heated at 50° C. overnight, and then cooled to room temperature. White solids were filtered off and discarded. Most of the solvent was removed from the filtrate by rotary evaporation. Ethyl acetate (800 mL) was added resulting in more precipitation. The white precipitate was removed by filtration. Solvent was removed from the filtrate by rotary evaporation and then under high vacuum at room temperature overnight to yield the title compound (211 g) as a thick oil. $^1$H NMR (400 MHz, DMSO-$d_6$): δ (ppm) 4.25 (t, 1H), 3.57 (s, 3H), 3.18 (s, 6H), 2.43 (m, 1H), 1.55-1.81 (m, 2H), 1.50-1.72 (m, 5H), 1.20-1.48 (m, 2H), 1.05-1.21 (m, 4H), 0.71-0.92 (m, 2H).

b. Potassium (S)-2-cyclohexylmethyl-4,4-dimethoxy-butyrate

Potassium hydroxide (289.6 g, 2322 mmol) was added to a solution of the product of the previous step (200.0 g, 0.77 mol) in methanol (700 mL) in one portion and the reaction mixture was stirred at RT for 20 h. Hydrogen chloride (130 mL, 1.5 mol) was added slowly until the reaction mixture had a pH ~8 (color change from greenish to orange) resulting in precipitation of fine solids. Solids were removed by filtration. Solvent was removed from the filtrate. Acetonitrile (1 L) was added to the crude product and the resulting slurry was stirred at room temperature overnight. The thick slurry was filtered, the filter cake was washed with acetonitrile (50 mL) and dried to yield a first crop of the title compound (133 g) as an off-white solid. Solvent was removed from the filtrate which was then dried under vacuum to yield about 100 g of a pasty solid. MTBE (500 mL) was added and the solids were stirred at RT overnight resulting in a thick slurry which was filtered and dried under high vacuum to yield a second crop of the title compound (82 g). $^1$H NMR (400 MHz, DMSO-$d_6$): δ (ppm) 4.28 (dd, 1H), 3.12 (s, 3H), 3.15 (s, 3H), 1.95 (m, 1H), 1.75 (m, 1H), 1.51-1.65 (m, 6H), 1.22-1.39 (m, 2H), 1.05-1.20 (m, 4H), 0.85-0.93 (m, 1H), 0.65-0.81 (m, 2H).

c: (S)-2-Cyclohexylmethyl-4,4-dimethoxy-butyric acid benzyl ester

Benzyl bromide (50.54 mL, 424.9 mmol) was added to a slurry of the product of the previous step (150.0 g, 531.1 mmol) in acetonitrile (2.0 L) in one portion and the heterogeneous reaction mixture was stirred at room temperature overnight. Additional benzyl bromide (5.05 mL, 42.49 mmol) was added and the reaction mixture was stirred at room temperature for 18 h. Solids were removed by filtration. The filtrate was dried by rotary evaporation and then under high vacuum overnight yielding the title compound (162 g). $^1$H NMR (400 MHz, DMSO-$d_6$): δ (ppm) 7.22-7.40 (m, 5H), 5.0-5.15 (q, 2H), 4.23 (t, 1H), 3.15 (s, 3H), 3.17 (s, 3H), 2.52 (m, 1H), 1.78 (m, 1H), 1.69 (m, 1H), 1.45-1.61 (m, 6H), 1.20-1.43 (m, 2H), 1.0-1.15 (m, 4H), 0.70-0.83 (m, 2H).

d. Sodium (S)-3-benzyloxycarbonyl-4-cyclohexyl-1-hydroxy-butane-1-sulfonate

To a mixture of the product of the previous step (160.0 g, 478.4 mmol) and acetonitrile (1.0 L) was added 1.0 M HCl in water (1.2 L) and the reaction mixture was heated at 35-40° C. for 2 h. Ethyl acetate (1.2 L) was added, phases were separated, and the organic layer was washed with brine (1 L). Sodium bisulfite (74.7 g, 718 mmol) was added to the wet organic layer and the reaction mixture was stirred at RT overnight. Most of the solvent was removed by rotary evaporation and acetonitrile (1 L) was added and the resulting slurry was stirred at RT overnight. The resulting thick white slurry was filtered, the filter cake was washed with acetonitrile (2×100 mL) and dried under vacuum to yield the title compound (200 g, >98% purity) as a white solid. $^1$H NMR (400 MHz, DMSO-$d_6$): δ (ppm) 7.23-7.41 (m, 5H), 5.30 (d, 1H), 4.98-5.18 (q, 2H), 3.75-3.88 (m, 1H), 3.60-3.79 (m, 1H), 2.05 (m, 0.5H), 1.45-1.82 (m, 2.5H), 1.45-1.60 (m, 5H), 1.20-1.42 (m, 2H), 1.0-1.17 (m, 4H), 0.69-0.82 (m, 2H).

EXAMPLE 1

(S)-4-((2S,3S)-7-Carbamoyl-1,1-diethyl-3-methoxy-1,2,3,4-tetrahydronaphthalen-2-ylamino)-2-cyclohexylmethyl-butyric acid a. (S)-4-((2S,3S)-7-Carbamoyl-1,1-diethyl-3-methoxy-1,2,3,4-tetrahydronaphthalen-2-ylamino)-2-cyclohexylmethyl-butyric acid methyl ester To a slurry of sodium (S)-4-cyclohexyl-1-hydroxy-3-methoxycarbonyl-butane-1-sulfonate (25.8 g, 81.5 mmol) and 2-methyl-tetrahydro-furan (300 mL) was added 1.0 M NaOH in water (76.1 mL) and the reaction mixture was stirred for 20 min at RT. To the reaction mixture was added (6S,7S)-7-amino-8,8-diethyl-6-methoxy-5,6,7,8-tetrahydro-naphthalene-2-carboxylic acid amide hydrochloride (17.0 g, 54.3 mmol); the reaction mixture was stirred for 40 min at RT, sodium triacetoxyborohydride (46.1 g, 217 mmol) was added in 4 portions. The reaction mixture was stirred at RT overnight after the first two portions. Water (200 mL) and MeTHF (100 mL) were added; the phases were separated and the organic layer was washed with 1 M NaOH (2×200 mL), diluted brine (200 mL) dried with $Na_2SO_4$ and solvent was removed to yield crude title intermediate (22 g) as a glassy yellow solid.

Crude product was purified by reverse-phase chromatography using a Microsorb 100-10 BDS 4 inch column. Crude product was dissolved in 1:1 acetonitrile: 1 M aq. HCl (150 mL) solvent mixture and eluted with water (0.1% HCl)/acetonitrile mobile phase (10-40% gradient). Pure fractions (>98%) were combined, most of the acetonitrile was removed by rotary evaporation, pH was adjusted to pH ~12 with solid $Na_2CO_3$ and purified product was extracted with MeTHF (3×1 L). Combined organic layers were dried with $Na_2SO_4$ and solvent removed to yield the title compound (16.5 g)

b. (S)-4-((2S,3S)-7-Carbamoyl-1,1-diethyl-3-methoxy-1,2,3,4-tetrahydronaphthalen-2-ylamino)-2-cyclohexylmethyl-butyric acid To a solution of (S)-4-((2S,3S)-7-carbamoyl-1,1-diethyl-3-methoxy-1,2,3,4-tetrahydro-naphthalen-2-ylamino)-2-cyclohexylmethyl-butyric acid methyl ester (12.0 g, 25.4 mmol) in methanol was added 5.0 M NaOH (25 mL) and the reaction mixture was heated at 30° C. for 8 h and then at 25° C. overnight. Most of the methanol solvent was removed by rotary evaporation at 25° C., water (100 mL) and isopropyl acetate (100 mL) was added and the resulting mixture was stirred for 15 min. The bottom two of three layers were extracted with isopropyl acetate (100 mL). Bottom layers were cooled to −5° C. and MeTHF (200 mL) was added and then concentrated HCl (~15 mL) was added in portions until pH ~2. Phases were separated, water layer was washed with MeTHF (100 mL) and combined organic layers were dried with $Na_2SO_4$. Most of the organic solvent was removed by rotary evaporation, ethyl acetate (200 mL) was added and the volume was reduced to 50 mL. Ethyl acetate (200 mL) was added and the resulting slurry was stirred/triturated at RT for 3 h. Product was filtered under nitrogen and dried under vacuum for 48 h to yield the hydrochloride salt of the title compound (11 g, 98.2% purity) as a white solid. $^1$H NMR (DMSO-d$_6$): δ (ppm) 0.54 (t, 3H), 0.63 (t, 3H), 0.82 (m, 2H), 1.05-1.3 (m, 6H), 1.45 (m, 1H), 1.55-2.0 (m, 10H), 2.40 (m, 1H), 2.67 (dd, 1H), 3.06 (m, 1H), 3.22 (m, 1H), 3.30 (dd, 1H), 3.41 (s, 3H), 3.45 (dd, 1H), 4.05 (m, 1H), 7.19 (d, 1H), 7.50 (br, 1H), 7.69 (d, 1 h), 7.70 (s, 1H), 7.95 (br, 2H), 9.26 (br, 1H).

EXAMPLE 2

(S)-4-((2S,3S)-7-Carbamoyl-1,1-diethyl-3-methoxy-1,2,3,4-tetrahydronaphthalen-2-ylamino)-2-cyclohexylmethyl-butyric acid (S)-4-((2S,3S)-7-Carbamoyl-1,1-diethyl-3-methoxy-1,2,3,4-tetrahydronaphthalen-2-ylamino)-2-cyclohexylmethyl-butyric acid hydrochloride (2.18 g, 4.40 mmol) was dissolved in methanol (30 mL) and water (30 mL) and 1.0 M NaOH (4.65 mL) was added. Methanol was removed by rotary evaporation resulting in precipitation and 1.0 M HCl (0.045 mL) was added resulting in additional precipitation. The solids were extracted with DCM: isopropyl alcohol (4:1, 3×40 mL) and dried over sodium sulfate. Water (30 mL) was added and the organics were removed by rotary evaporation providing a gummy precipitate in water. Acetonitrile (25 mL) was added and the reaction mixture was lyophilized to provide the title compound as an amorphous solid. (1.99 g).

EXAMPLE 3

Crystalline (S)-4-((2S,3S)-7-Carbamoyl-1,1-diethyl-3-methoxy-1,2,3,4-tetrahydronaphthalen-2-ylamino)-2-cyclohexylmethyl-butyric acid a. (S)-4-((2S,3S)-7-Carbamoyl-1,1-diethyl-3-methoxy-1,2,3,4-tetrahydronaphthalen-2-ylamino)-2-cyclohexylmethyl-butyric acid benzyl ester hydrochloride To a suspension of sodium (S)-3-benzyloxycarbonyl-4-cyclohexyl-1-hydroxy-butane-1-sulfonate (160 g, 400 mmol), the product of Preparation 8, in MeTHF (2.0 L) and water (600 mL) was added 1.0 M NaOH in water (400 mL) and the reaction mixture was stirred at room temperature for 90 min. Phases were separated and the solution was concentrated to a volume of ~300 mL.

The resulting concentrated solution was added to a slurry of (6S,7S)-7-amino-8,8-diethyl-6-methoxy-5,6,7,8-tetrahydro-naphthalene-2-carboxylic acid amide hydrochloride (100.0 g, 319.7 mmol) in DMF (1 L). Resulting slurry was stirred at room temperature for 2 h, the reaction mixture was cooled to 0° C. followed by portion-wise addition of sodium triacetoxyborohydride (169 g, 799 mmol) over 15 min. The reaction mixture was stirred at RT overnight, cooled to 10° C. and then 1.0 M NaOH in water (3 L) and ethyl acetate (5 L) were added. The reaction mixture was stirred for 10 min, phases were separated, and the organic layer was washed with diluted brine (1:1, 2 L). To the organic layer was added 1.0 M HCl in water (520 mL, 520 mmol) and most of the ethyl acetate was removed by rotary evaporation. Water (500 mL) and ethanol (1 L) were added and the volume was slowly reduced by rotary evaporation to ~1 L. The resulting off-white free-flowing slurry was stirred at RT overnight. Product was isolated by filtration, flask and filter cake were washed with water (2×200 mL) and then dried to yield the title compound (175 g) as a white solid (~99% purity, 90% yield based on aminotetralin reagent). $^1$H NMR (400 MHz, DMSO-d$_6$): δ (ppm) 9.33 (br, 1H), 8.09 (br, 1H), 7.98 (s, 1H), 7.70 (s, 1H), 7.68 (d, 1H), 7.28-7.36 (m, 2H), 7.19 (d, 1H), 5.10 (q, 2H), 4.04 (m, 1H), 3.45 (dd, 1H), 3.38 (s, 3H), 3.25 (m, 2H), 3.05 (m, 1H), 2.62 (m, 2H), 1.95-2.15 (m, 2H), 1.61-1.82 (m, 3H), 1.50-1.61 (m, 4H), 1.42-1.50 (m, 1H), 1.24-1.32 (m, 1H), 0.98-1.18 (m, 4H), 0.71-0.89 (m, 2H), 0.63 (t, 3H), 0.52 (t, 3H)

b. Crystalline (S)-4-((2S,3S)-7-Carbamoyl-1,1-diethyl-3-methoxy-1,2,3,4-tetrahydro-naphthalen-2-ylamino)-2-cyclohexylmethyl-butyric acid The product of the previous step (175.0 g, 299 mmol) was partitioned between ethyl acetate (2.5 L), water (1 L) and 1.0 M NaOH in water (300 mL, 299 mmol). Phases were separated, the organic layer was washed with diluted brine (1:1, 250 mL), and dried with sodium sulfate. Solvent was removed by rotary evaporation and the resulting product dried overnight under high vacuum to provide the free-base intermediate (S)-4-((2S,3S)-7-carbamoyl-1,1-diethyl-3-methoxy-1,2,3,4-tetrahydro-naphthalen-2-ylamino)-2-cyclohexylmethyl-butyric acid benzyl ester (~160 g) as a sticky solid.

The free-base intermediate was dissolved in a mixture of acetonitrile (1.6 L) and water (300 mL). To half of the solution (1 L) was added 10% palladium (10 g, 9 mmol) on carbon (wet). The reaction mixture was purged with nitrogen and then with hydrogen for 2 min and then exposed to 10-15 psi H$_2$ for 3 h at RT. The reaction mixture was filtered through celite, and the flask and filter cake were washed with acetonitrile (50 mL). The yellowish filtrate was stirred with thiol-modified silica (10 g) at RT for 2 h and then filtered through celite. Most of the solvent was removed by rotary evaporation at 25° C. Acetonitrile (500 mL) was added and most of the solvent was removed by rotary evaporation. Additional acetonitrile (500 mL) was added resulting in fast precipitation of sticky solids. The reaction mixture was stirred vigorously at room temperature overnight resulting in a free-flowing off-white slurry. Product was isolated by filtration; the filter cake was washed with acetonitrile (2×50 mL) and then dried under vacuum to yield the crystalline title compound (56 g, 98.8% purity). Water content 0.49% (w/w). $^1$H NMR (400 MHz, DMSO-d$_6$): δ (ppm) 7.89 (br, 1H), 7.65 (s, 1H), 7.60 (d, 1H), 7.22 (br, 1H), 7.11 (d, 1H), 3.55 (m, 1H), 3.38 (s, 3H), 3.25 (dd, 1H), 2.95 (m, 1H), 2.59 (d, 1H), 2.49 (m, 2H), 1.81 (m, 2H), 1.49-1.63 (m, 5H), 1.41-1.50 (m, 2H), 1.05-1.25 (m, 4H), 0.72-0.90 (m, 2H), 0.45 (t, 3H), 0.57 (t, 3H).

Note: In the text of the following examples (S)-4-((2S,3S)-7-Carbamoyl-1,1-diethyl-3-methoxy-1,2,3,4-tetrahydronaphthalen-2-ylamino)-2-cyclohexylmethyl-butyric acid is referenced as compound 1.

EXAMPLE 4

Crystallization of (S)-4-((2S,3S)-7-Carbamoyl-1,1-diethyl-3-methoxy-1,2,3,4-tetrahydronaphthalen2-ylamino)-2-cyclohexylmethyl-butyric acid (Form I)

Amorphous compound 1 (100 mg, 0.22 mmol) was dissolved in isopropanol (0.83 mL). After four days, crystals were observed in the solution. The mother liquor was decanted and 1:1 acetonitrile:ethyl acetate (0.2 mL and then an additional 0.3 mL) was added to provide a slurry of the title compound.

EXAMPLE 5

Crystallization of (S)-4-((2S,3S)-7-Carbamoyl-1,1-diethyl-3-methoxy-1,2,3,4-tetrahydronaphthalen-2-ylamino)-2-cyclohexylmethyl-butyric acid (Form I)

Amorphous compound 1 (33 mg, 0.072 mmol) was dissolved in a premixed solution of acetonitrile (0.04 mL), 1-propanol (0.0605 mL), and water (0.0035 mL) and the process mixture was stirred at RT overnight. A precipitate started to form in less than about 1 h. The solids were collected by filtration, washed with 3:2 acetonitrile:isopropanol (2 mL) and dried under vacuum to provide the title compound.

EXAMPLE 6

Crystallization of (S)-4-((2S,3S)-7-Carbamoyl-1,1-diethyl-3-methoxy-1,2,3,4-tetrahydronaphthalen-2-ylamino)-2-cyclohexylmethyl-butyric acid (Form I)

Amorphous compound 1 (84.2 mg, 0.18 mmol) was dissolved in a mixture of water (0.003 mL) and methanol (0.027 mL) and then a mixture of water (0.013 mL) and acetonitrile (0.090 mL) was added. Crystals were observed within 2 min. The process mixture was held for 3 days at RT without stirring. The mother liquor was decanted and the solids were isolated by vacuum filtration and washed with acetonitrile to provide the title compound (54 mg, 64% yield).

EXAMPLE 7

Crystallization of (S)-4-((2S,3S)-7-Carbamoyl-1,1-diethyl-3-methoxy-1,2,3,4-tetrahydronaphthalen-2-ylamino)-2-cyclohexylmethyl-butyric acid (Form II)

Amorphous compound 1 (70 mg, 0.15 mmol) was dissolved in a premixed solution of acetonitrile (0.136 mL) and isopropanol (0.090 mL) and the process mixture was stirred at RT overnight. A precipitate started to form in less than about 1 h. The solids were collected by filtration, washed with 3:2 acetonitrile:isopropanol (2 mL) and dried under vacuum to provide the title compound (64 mg).

EXAMPLE 8

Crystallization of (S)-4-((2S,3S)-7-Carbamoyl-1,1-diethyl-3-methoxy-1,2,3,4-tetrahydronaphthalen-2-ylamino)-2-cyclohexylmethyl-butyric acid hydrochloride Amorphous hydrochloride salt of compound 1 (56.7 mg, 0.12 mmol) was dispersed in diethylene glycol dimethylether (DEGDME) (0.50 mL), heated to 50° C. for 20 min and slowly cooled overnight. The process mixture was left at ambient temperature for 11 days. Resulting crystals were isolated and washed with DEGDME (~0.1 mL) to provide the title compound.

EXAMPLE 9

Crystallization of (S)-4-((2S,3S)-7-Carbamoyl-1,1-diethyl-3-methoxy-1,2,3,4-tetrahydronaphthalen-2-ylamino)-2-cyclohexylmethyl-butyric acid hydrochloride Amorphous hydrochloride salt of compound 1 (72.2 mg, 0.15 mmol) was dispersed in ethyl acetate (1.0 mL), sonicated for less than 1 min, heated to 50° C. and slowly cooled. The process mixture was left at ambient temperature for 3 days. Resulting crystals were isolated to provide the title compound.

EXAMPLE 10

Crystallization of (S)-4-((2S,3S)-7-Carbamoyl-1,1-diethyl-3-methoxy-1,2,3,4-tetrahydronaphthalen-2-ylamino)-2-cyclohexylmethyl-butyric acid hydrochloride Amorphous hydrochloride salt of compound 1 (50 mg, 0.11 mmol) was dispersed in ethyl acetate (0.5 mL) and stirred at RT for 4 days. The resulting crystals were isolated to provide the title compound (30 mg).

EXAMPLES 11-15

Properties of Solid Forms of the Invention

Samples of crystalline (S)-4-((2S,3S)-7-carbamoyl-1,1-diethyl-3-methoxy-1,2,3,4-tetrahydro-naphthalen-2-ylamino)-2-cyclohexylmethyl-butyric acid (compound 1) prepared in Examples 3 and 7 and of the crystalline hydrochloride salt of compound 1, prepared in Example 9, as well as a sample of crystalline (S)-4-((2S,3S)-7-Carbamoyl-1,1-diethyl-3-methoxy-1,2,3,4-tetrahydro-naphthalen-2-ylamino)-2-cyclohexylmethyl-butyric acid benzyl ester hydrochloride, (hydrochloride salt of compound 2), prepared as in Example 3a were analyzed by x-ray powder diffraction (XRPD), differential scanning calorimetry (DSC), and thermogravimetric analysis (TGA).

EXAMPLE 11

X-Ray Powder Diffraction

Figure 4:
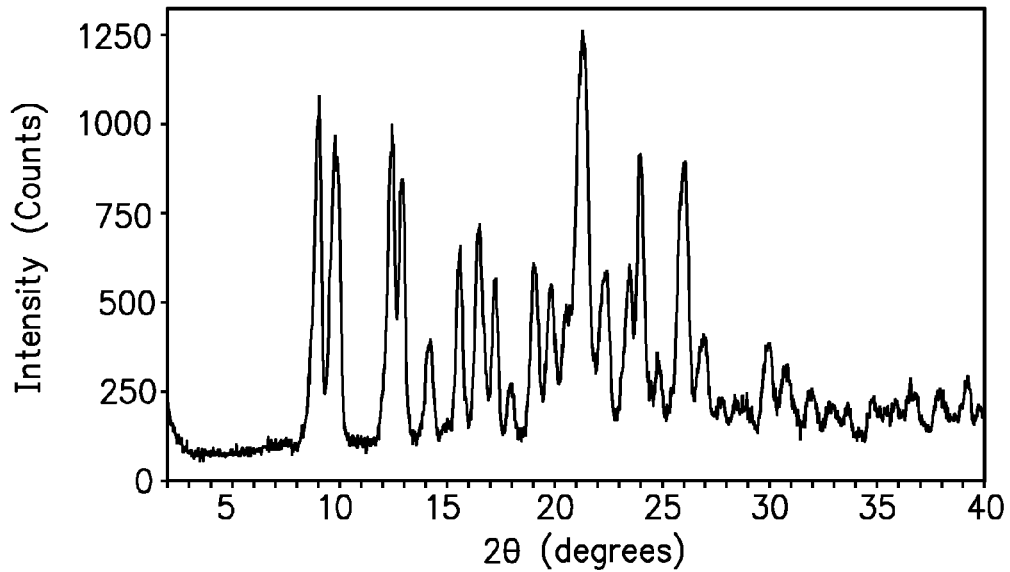
FIG. 4 shows an x-ray powder diffraction (XRPD) pattern of crystalline Form II (S)-4-((2S,3S)-7-carbamoyl-1,1-diethyl-3-methoxy-1,2,3,4-tetrahydronaphthalen-2-ylamino)-2-cyclohexylmethyl-butyric acid of the invention.
Figure 6:
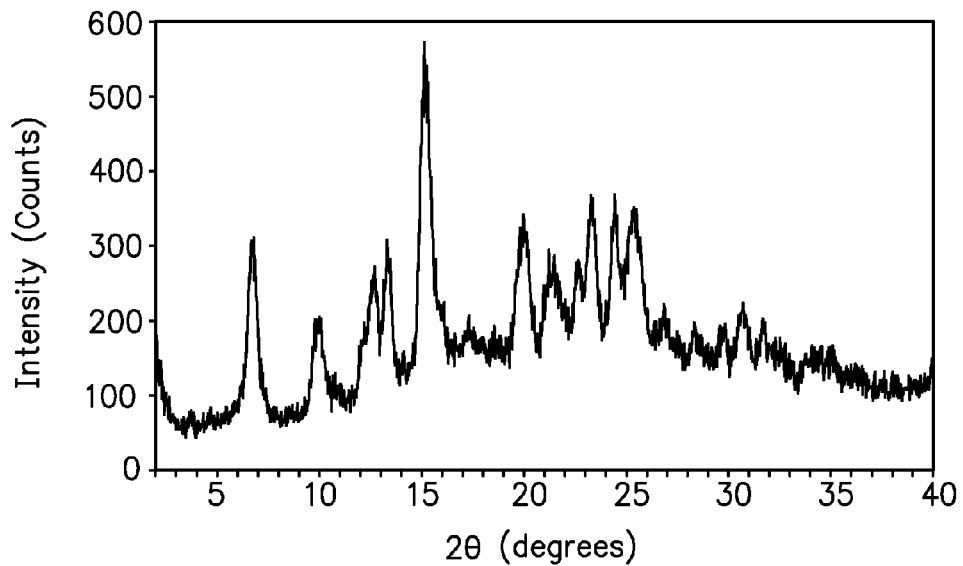
FIG. 6 shows an x-ray powder diffraction (XRPD) pattern of a crystalline hydrochloride salt of (S)-4-((2S,3S)-7-carbamoyl-1,1-diethyl-3-methoxy-1,2,3,4-tetrahydronaphthalen-2-ylamino)-2-cyclohexylmethyl-butyric acid of the invention.
Figure 8:
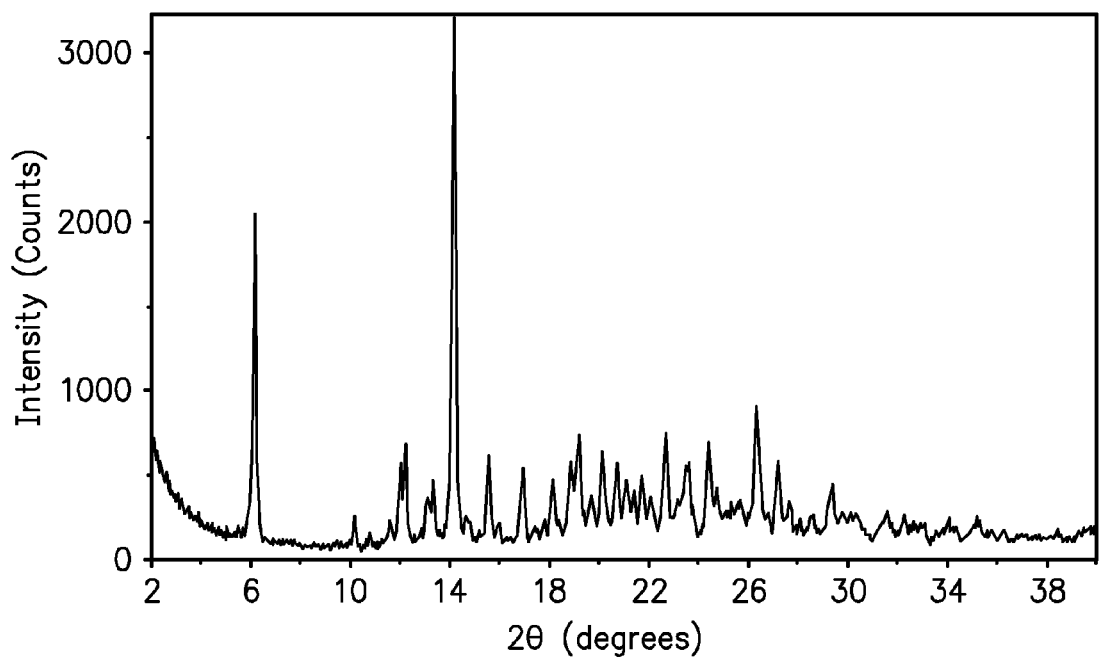
FIG. 8 shows an x-ray powder diffraction (XRPD) pattern of a crystalline hydrochloride salt of (S)-4-((2S,3S)-7-carbamoyl-1,1-diethyl-3-methoxy-1,2,3,4-tetrahydronaphthalen-2-ylamino)-2-cyclohexylmethyl-butyric acid benzyl ester of the invention.
Figure 9:
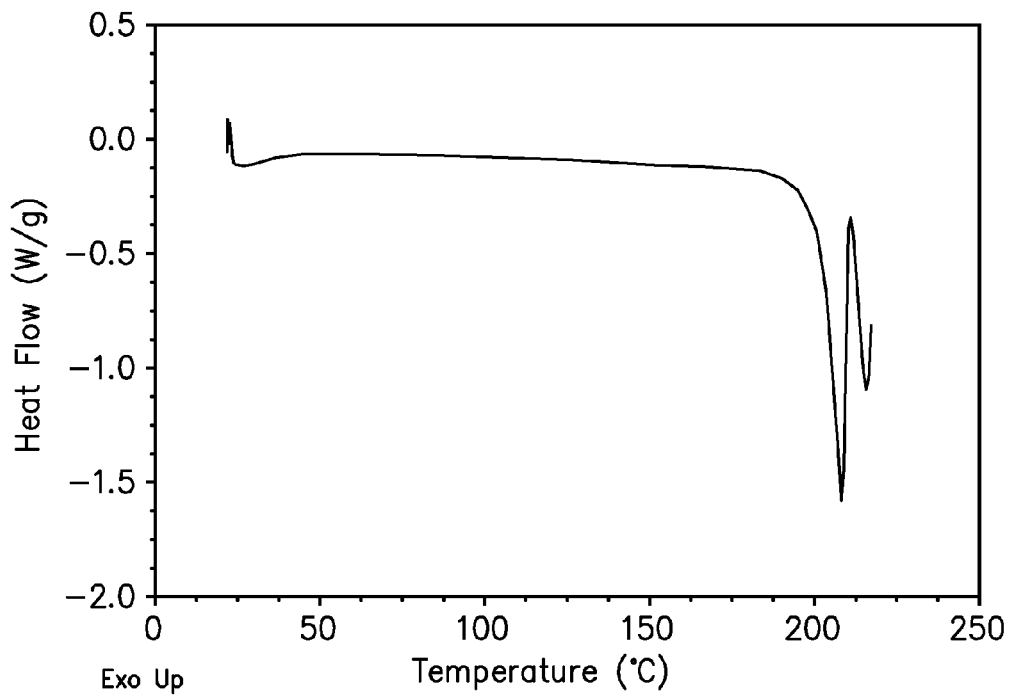
FIG. 9 shows a differential scanning calorimetry (DSC) trace of a crystalline hydrochloride salt of (S)-4-((2S,3S)-7-carbamoyl-1,1-diethyl-3-methoxy-1,2,3,4-tetrahydronaphthalen-2-ylamino)-2-cyclohexylmethyl-butyric acid benzyl ester of the invention.

X-ray powder diffraction patterns of FIGS. 1, 4, and 6 were obtained with a Rigaku diffractometer using Cu Kα (30.0 kV, 15.0 mA) radiation. The analysis was performed with the goniometer running in continuous-scan mode of 2° per min (FIG. 1) or 3° per min (FIGS. 4, 6, and 8) with a step size of 0.03° over a range of 2 to 40°. Samples were prepared on quartz specimen holders as a thin layer of powdered material. The instrument was calibrated with a silicon standard. FIG. 8 was obtained with a Thermo XTRA model ARL diffractometer scanning at 1.22° per min with a step size of 0.03° over a range of 2 to 40°.

EXAMPLE 12

Thermal Analysis

Differential scanning calorimetry (DSC) was performed using a TA Instruments Model Q-100 module. Data were collected and analyzed using TA Instruments Thermal Advantage for Q Series™ software. A sample of about 1-10 mg was accurately weighed into an aluminum pan with lid. The sample was evaluated using a linear heating ramp of 10° C./min from 5° C. to, typically, 265° C. The DSC cell was purged with dry nitrogen during use. Representative DSC traces for samples of crystalline Form I and Form II, of the crystalline hydrochloride salt of compound 1, as well as the crystalline hydrochloride salt of compound 2, are shown in FIGS. 2, 5, 7, and 9 respectively.

Figure 2:
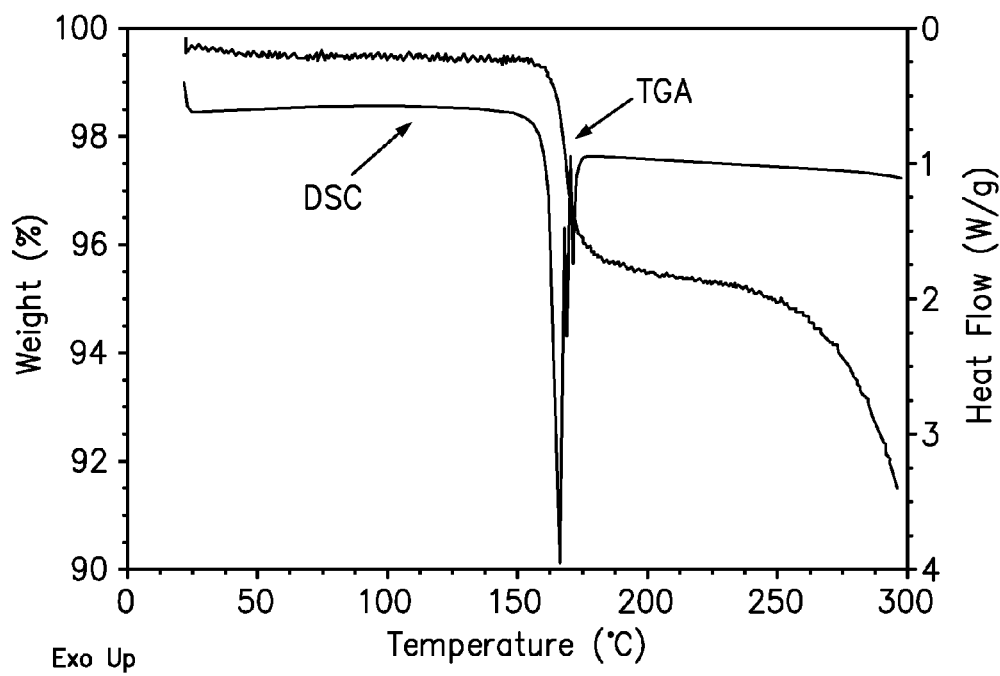
FIG. 2 shows a differential scanning calorimetry (DSC) trace (right side vertical axis) and a thermal gravimetric analysis (TGA) trace (left side vertical axis) of crystalline Form I (S)-4-((2S,3S)-7-carbamoyl-1,1-diethyl-3-methoxy-1,2,3,4-tetrahydronaphthalen-2-ylamino)-2-cyclohexylmethyl-butyric acid of the invention.

Thermogravimetric analysis (TGA) was performed using a TA Instruments Model Q-500 module. Data were collected and analyzed using TA Instruments Thermal Advantage for Q Series™ software. A sample weighing about 1-5 mg was placed in an aluminum pan on a platinum cradle and scanned from ambient temperature to 300° C. with a linear heating rate of 10° C./min. The balance and furnace chambers were purged with nitrogen during use. Representative TGA traces for samples of crystalline Form I and of a crystalline hydrochloride salt of compound 1 are also shown in FIGS. 2 and 7, respectively.

EXAMPLE 13

Dynamic Moisture Sorption Assessment

Dynamic moisture sorption (DMS) assessment was performed at 25° C. using a VTI atmospheric microbalance, SGA-100 system (VTI Corp., Hialeah, Fla. 33016). A sample size of approximately 5-10 mg was used and the humidity was set at the ambient value at the start of the analysis. A typical DMS analysis consisted of three or four scans: ambient to 2% relative humidity (RH), 2% RH to 90% RH, 90% RH to 5% RH at a scan rate of 5% RH/step, and, in some case a second adsorption 2% RH to 90% RH. The mass was measured every two minutes and the RH was changed to the next value (±5% RH) when the mass of the sample was stable to within 0.02% for 5 consecutive points. A representative DMS trace for a sample of crystalline Form I prepared in Example 3 is shown in FIG. 3.

EXAMPLE 14

X-ray Diffraction Crystal Structure Analysis

A needle-like crystal of crystalline Form I having dimensions of 0.20×0.10×0.06 mm, prepared in Example 6, was analyzed. X-ray diffraction crystal structure data was obtained using a Nonius Kappa-CCD diffractometer using Mo K$_\alpha$ radiation. Full sphere data was collected up to θ=27.5 degrees at a temperature of 120° K. and was analyzed using SHELX-97 software. The following lattice parameters were derived: unit cell is orthorhombic with dimensions a=7.546 Å, b=17.003 Å, c=20.628 Å, cell volume (V) of 2646.7 Å$^3$; calculated density is 1.151 g/cm$^3$; space group is P2$_1$2$_1$2$_1$. Powder x-ray diffraction peaks predicted from the derived atomic positions were judged by visual inspection to be in excellent agreement with the experimentally determined peak positions.

Assay 1: Radioligand Binding Assay on Human Mu, Human Delta and Guinea Pig Kappa Opioid Receptors
a. Membrane Preparation CHO-K1 (Chinese Hamster Ovary) cells stably transfected with human mu opioid or with guinea pig kappa receptor cDNA were grown in medium consisting of Ham's-F12 media supplemented with 10% FBS, 100 units/ml penicillin-100 µg/mL streptomycin and 800 µg/mL Geneticin in a 5% CO$_2$, humidified incubator @ 37° C. Receptor expression levels (B$_{max}$ ~2.0 and ~0.414 µmol/mg protein, respectively) were determined using [$^3$H]-Diprenorphine (specific activity~50-55 Ci/mmol) in a membrane radioligand binding assay.

Cells were grown to 80-95% confluency (<25 subculture passages). For cell line passaging, the cell monolayer was incubated for 5 minutes at room temperature and harvested by mechanical agitation in 10 mL of PBS supplemented with 5 mM EDTA. Following resuspension, cells were transferred to 40 mL fresh growth media for centrifugation for 5 minutes at 1000 rpm and resuspended in fresh growth medium at the appropriate split ratio.

For membrane preparation, cells were harvested by gentle mechanical agitation with 5 mM EDTA in PBS followed by centrifugation (2500 g for 5 minutes). The pellets were resuspended in Assay Buffer (50 mM 4-(2-hydroxyethyl)piperazine-1-ethanesulfonic acid N-(2-hydroxyethyl)piperazine-N'-(2-ethanesulfonic acid) (HEPES)), pH 7.4, and homogenized with a polytron disrupter on ice. The resultant homogenates were centrifuged (1200 g for 5 minutes), the pellets discarded and the supernatant centrifuged (40,000 g for 20 minutes). The pellets were washed once by resuspension in Assay Buffer, followed by an additional centrifugation (40,000 g for 20 minutes). The final pellets were resuspended in Assay Buffer (equivalent 1 T-225 flask/1 mL assay buffer). Protein concentration was determined using a Bio-Rad Bradford Protein Assay kit and membranes were stored in frozen aliquots at −80° C., until required.

Human delta opioid receptor (hDOP) membranes were purchased from Perkin Elmer. The reported K$_d$ and B$_{max}$ for these membranes determined by saturation analyses in a [$^3$H]-Natrindole radioligand binding assays were 0.14 nM (pK$_d$=9.85) and 2.2 µmol/mg protein, respectively. Protein concentration was determined using a Bio-Rad Bradford Protein Assay kit. Membranes were stored in frozen aliquots at −80° C., until required.
b. Radioligand Binding Assays Radioligand binding assays were performed in an Axygen 1.1 mL deep well 96-well polypropylene assay plate in a total assay volume of 200 µL containing the appropriate amount of membrane protein (~3, ~2 and ~20 µg for mu, delta and kappa, respectively) in Assay Buffer, supplemented with 0.025% bovine serum albumin (BSA). Saturation binding studies for determination of K$_d$ values of the radioligand were performed using [$^3$H]-Diprenorphine at 8-12 different concentrations ranging from 0.001 nM-5 nM. Displacement assays for determination of pKi values of compounds were performed with [$^3$H]-Diprenorphine at 0.5, 1.2, and 0.7 nM for mu, delta, and kappa, respectively, and eleven concentrations of compound ranging from 10 pM-100 µM.

Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM naloxone. K$_i$ values for test compounds were calculated, in Prism, from the best fit IC$_{50}$ values, and the K$_d$ value of the radioligand, using the Cheng-Prusoff equation (K$_i$=IC$_{50}$/(1+([L]/K$_d$)) where [L]=the concentration of [$^3$H]-Diprenorphine. Results are expressed as the negative decadic logarithm of the K$_i$ values, pK$_i$.

Test compounds having a higher pK$_i$ value in these assays have a higher binding affinity for the mu, delta, or kappa opioid receptor. Compound 1 exhibited a pK$_i$ value of 9.4 at the human mu opioid receptor.

Assay 2: Agonist Mediated Activation of the Mu-Opioid Receptor in Membranes Prepared from CHO-K1 Cells Expressing the Human Mu-Opioid Receptor In this assay, the potency and intrinsic activity values of test compounds were determined by measuring the amount of bound GTP-Eu present following receptor activation in membranes prepared from CHO-K1 cells expressing the human mu opioid receptor.
a. Mu Opioid Receptor Membrane Preparation:

Human mu opioid receptor (hMOP) membranes were either prepared as described above or were purchased from Perkin Elmer. The reported $pK_d$ and $B_{max}$ for the purchased membranes determined by saturation analyses in a [$^3$H]-Diprenorphine radioligand binding assays was 10.06 and 2.4 µmol/mg protein, respectively. Protein concentration was determined using a Bio-Rad Bradford Protein Assay kit. Membranes were stored in frozen aliquots at −80° C., until required. Lyophilized GTP-Eu and GDP were diluted to 10 µM and 2 mM, respectively, in double distilled H$_2$O then mixed and permitted to sit at room temperature for 30 minutes prior to transfer to individual aliquots samples for storage at −20° C.

b. Human mu GTP-Eu Nucleotide Exchange Assay

GTP-Eu nucleotide exchange assays were performed using the DELPHIA GTP-binding kit (Perkin/Elmer) in AcroWell 96 well filter plates according to the manufacturer's specifications. Membranes were prepared as described above, and prior to the start of the assay, aliquots were diluted to a concentration of 200 µg/mL in Assay Buffer (50 mM HEPES, pH 7.4 at 25° C.), then homogenized for 10 seconds using a Polytron homogenizer. Test compounds were received as 10 mM stock solutions in DMSO, diluted to 400 µM into Assay Buffer containing 0.1% BSA, and serial (1:5) dilutions then made to generate ten concentrations of compound ranging from 40 pM-80 µM-GDP and GTP-Eu were diluted to 4 µM and 40 nM, respectively, in Assay Buffer. The assay was performed in a total volume of 100 µL containing 5 µg of membrane protein, test compound ranging from 10 µM-20 µM), 1 µM GDP, and 10 nM GTP-Eu diluted in 10 mM MgCl$_2$, 50 mM NaCl, and 0.0125% BSA, (final assay concentrations). A DAMGO (Tyr-D-Ala-Gly-(methyl)Phe-Gly-ol) concentration-response curve (ranging from 12.8 pM-1 µM) was included on every plate.

Assay plates were prepared immediately prior to assay following the addition of 25 µL of Assay Buffer, 25 µL of test compound, and 25 µL GDP and GTP-Eu. The assay was initiated by the addition of 25 µL membrane protein and allowed to incubate for 30 minutes. The assay plates were then filtered with a Waters vacuum manifold connected to the house vacuum regulated to 10-12 in. Hg and washed with room temperature GTP Wash Solution (2×300 mL). The bottoms of the plates were blotted to remove excess liquid. The plates were then immediately read to determine the amount of bound GTP-Eu by measuring Time Resolved Fluorescence (TRF) on a Packard Fusion Plate ReaderVehicle: DMSO not to exceed 1% final assay concentration.

The amount of bound GTP-Eu is proportional to the degree of activation of the mu opioid receptors by the test compound. The intrinsic activity (IA), expressed as a percentage, was determined as the ratio of the amount of bound GTP-Eu observed for activation by the test compound to the amount observed for activation by DAMGO which is presumed to be a full agonist (IA=100). Compound 1 demonstrated an intrinsic activity of −8 in this assay. Thus, the present active agent has been shown to be an antagonist.

Assay 3: Rat Model of In Vivo Efficacy

In this assay the efficacy of test compounds was evaluated in a model of gastrointestinal transit, which evaluates peripheral activity. This study was approved by the Institutional Animal Care and Use Committee at Theravance, Inc. and conformed to the Guide for the Care and Use of Laboratory Animals published by the National Academy of Sciences (©1996).

a. Rat Gastric Emptying Assay

Test compounds were evaluated in the rat gastric emptying assay to determine their ability to reverse loperamide-induced delayed gastric emptying. Rats were fasted up overnight prior to administration of test compounds or vehicle by intravenous, subcutaneous, intramuscular or oral routes of administration at doses ranging from 0.001 to about 30 milligrams/kilogram (mg/kg). The administration of test compound was followed by subcutaneous administration of loperamide at a dose of 1 mg/kg or vehicle. Five minutes post loperamide or vehicle administration, a non-nutritive, non-absorbable charcoal meal was administered via oral gavage and animals were allowed free access to water for the sixty minute duration of the experiment. Animals were then euthanized via carbon dioxide asphyxiation followed by thoracotomy and the stomach was carefully excised. The stomach was ligated at the lower esophageal sphincter and the pyloric sphincter to prevent additional emptying during tissue removal. Gastric weight was then determined after removal of the ligatures.

b. Data Analysis and Results

Data was analyzed using the GraphPad Prism Software package (GraphPad Software, Inc., San Diego, Calif.). Percent reversal curves were constructed by non-linear regression analysis using the sigmoidal dose response (variable slope) model and best-fit ID$_{50}$ values were calculated. Curve minima and maxima were fixed to loperamide control values (indicating 0% reversal) and vehicle controls (indicating 100% reversal), respectively. Results are expressed as ID$_{50}$, the dose required for 50% reversal of the effects of loperamide, in milligrams per kilogram. Compound 1, administered orally, exhibited an ID$_{50}$ value of 0.09 mg/kg in the gastric emptying model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A crystalline solid form of (S)-4-((2S,3S)-7-carbamoyl-1,1-diethyl-3-methoxy-1,2,3,4-tetrahydronaphthalen-2-ylamino)-2-cyclohexylmethyl-butyric acid, wherein the crystalline solid form is characterized by an x-ray powder diffraction pattern having diffraction peaks at 2θ values of 6.92±0.20 and 15.34±0.20, and having two or more diffraction peaks at 2θ values selected from 10.24±0.20, 11.48±0.20, 12.32±0.20, 13.46±0.20, 14.04±0.20, 17.30±0.20, 18.06±0.20, 20.30±0.20, 21.42±0.20, 23.48±0.20, 25.54±0.20, 26.96±0.20, 29.30±0.20, and 30.72±0.20.

2. The crystalline solid form of claim 1, wherein the x-ray powder diffraction pattern comprises diffraction peaks at 2θ values of 6.92±0.20 and 15.34±0.20 and two or more diffraction peaks at 2θ values selected from 10.24±0.20, 13.46±0.20, 18.06±0.20, and 21.42±0.20.

3. The crystalline solid form of claim 1, wherein the crystalline solid form is characterized by an x-ray powder diffraction pattern in which the peak positions are in accordance with the peak positions of the pattern shown in FIG. 1.

4. The crystalline solid form of claim 1, wherein the crystalline solid form is characterized by a differential scanning calorimetry trace recorded at a heating rate of 10° C. per minute which shows a maximum in endothermic heat flow at a temperature between about 162° C. and about 170° C.

5. The crystalline solid form of claim 1, wherein the crystalline solid form is characterized by a differential scanning calorimetry trace in accordance with that shown in FIG. 2.

6. A pharmaceutical composition comprising a pharmaceutically acceptable carrier and the crystalline solid form of claim 1.

* * * * *